(12) United States Patent
Heldman et al.

(10) Patent No.: US 11,389,157 B2
(45) Date of Patent: Jul. 19, 2022

(54) WOUND CLOSURE ASSEMBLIES AND METHODS FOR APPROXIMATING TISSUE

(71) Applicant: Mentor Worldwide LLC, Irvine, CA (US)

(72) Inventors: Lucas Heldman, Wayne, NJ (US); Michael Hoffman, Hillsborough, NJ (US)

(73) Assignee: Mentor Worldwide LLC, Irvine, CA (US)

( * ) Notice: Subject to any disclaimer, the term of this patent is extended or adjusted under 35 U.S.C. 154(b) by 228 days.

(21) Appl. No.: 16/884,178

(22) Filed: May 27, 2020

(65) Prior Publication Data

US 2021/0369268 A1    Dec. 2, 2021

(51) Int. Cl.
*A61B 17/06* (2006.01)
*A61B 17/04* (2006.01)

(52) U.S. Cl.
CPC .. *A61B 17/06066* (2013.01); *A61B 17/06166* (2013.01); *A61B 17/0482* (2013.01); *A61B 2017/0409* (2013.01); *A61B 2017/0608* (2013.01)

(58) Field of Classification Search
CPC .............. A61B 17/06; A61B 17/06114; A61B 17/0401; A61B 17/0482; A61B 17/06066; A61B 2017/0409; A61B 2017/0608
See application file for complete search history.

(56) References Cited

U.S. PATENT DOCUMENTS

| 3,160,157 A | 12/1964 | Chisman |
| 5,626,614 A | 5/1997 | Hart |
| 5,814,070 A | 9/1998 | Borzone et al. |
| 8,771,314 B2 | 7/2014 | Crombie et al. |
| 9,173,652 B2 | 11/2015 | Lombardo et al. |

(Continued)

FOREIGN PATENT DOCUMENTS

| EP | 0908143 | 4/1999 |
| EP | 2419027 | 4/2014 |

(Continued)

OTHER PUBLICATIONS

International Search Report issued in corresponding International Application No. PCT/IB2021/054281, dated Aug. 13, 2021, 6 pages.

*Primary Examiner* — Tuan V Nguyen
(74) *Attorney, Agent, or Firm* — Doherty IP Law Group LLC

(57) ABSTRACT

A wound closure assembly includes an insertion tool having a proximal end and a distal section, such as a curved distal section, having a penetrating tip and first and second notches that are formed on opposite sides of the distal section. The assembly includes a tissue anchor having a hollow body and an insertion tool channel extending through the hollow body. First and second spaced tips project distally from the distal end of the hollow body and oppose one another on opposite sides of the insertion tool channel. The distal section of the insertion tool is inserted into the insertion tool channel of the tissue anchor so that the penetrating tip is distal to the first and second spaced tips, with the first and second spaced tips nested within the first and second notches for generating a releasable interference fit between the tissue anchor and the insertion tool.

21 Claims, 24 Drawing Sheets

(56) References Cited

U.S. PATENT DOCUMENTS

| | | | |
|---|---|---|---|
| 9,198,648 B2 | 12/2015 | Crombie et al. | |
| 9,402,616 B2 | 8/2016 | Harris et al. | |
| 10,028,739 B2* | 7/2018 | Alexander | A61B 17/0643 |
| 10,299,782 B2* | 5/2019 | Sengun | A61B 17/0469 |
| 2007/0191870 A1* | 8/2007 | Baker | A61F 5/0086 |
| | | | 606/153 |
| 2008/0109038 A1 | 5/2008 | Steiner et al. | |
| 2012/0259168 A1* | 10/2012 | Goldberg | A61B 17/06109 |
| | | | 600/30 |
| 2012/0323275 A1* | 12/2012 | Crombie | A61B 17/0401 |
| | | | 606/232 |
| 2014/0018827 A1 | 1/2014 | Leiber | |

FOREIGN PATENT DOCUMENTS

| | | |
|---|---|---|
| WO | 2009158246 | 12/2009 |
| WO | 2012072087 | 6/2012 |
| WO | 2012072244 | 6/2012 |
| WO | 2012177548 | 12/2012 |

\* cited by examiner

WOUND CLOSURE ASSEMBLIES AND METHODS FOR APPROXIMATING TISSUE

BACKGROUND OF THE INVENTION

Field of the Invention

The present patent application is generally related to the field of surgery, and is more particularly related to systems, devices and methods used for suturing tissue and approximating tissue planes.

Description of the Related Art

During certain surgical procedures, such as abdominoplasty, open ventral hernia repair, flap harvesting, deep tissue closure, and skin closure, tissue planes are separated. At the conclusion of the surgical procedures, the separated tissue planes must be reunited such as by suturing the tissue planes. Although the goal of tissue plane approximation is that the tissue planes heal and reunite normally, it is often not the case. Seroma formation (i.e., fluid build-up in the space between the tissue planes) is a typical complication. When approximating tissue planes with traditional techniques, dead spaces are often formed between the tissue planes, which allows for tissue shear, which, in turn, increases the risk of developing a seroma and an infection.

Attempts to minimize tissue seroma include implanting drains to remove fluid from the space between the tissue planes. Although using drains is somewhat effective, this method does not affect the formation of the fluid pockets, but rather removes the fluid as it is produced. Other attempts to minimize the likelihood of seroma formation include tissue fixation methods such as suture quilting and progressive tension suturing (PTS). Both of these methods (i.e., suture quilting and PTS) involve placing a large number of individual sutures progressively along the tissue planes, which is intricate and very time consuming. These tissue fixation methods also have other drawbacks, including accessibility, tension control, security, consistency, and cheese-wiring (i.e., suture cutting through tissue).

There have been some efforts directed to improving the systems, devices, and methods that are used for approximating tissue planes. For example, U.S. Pat. No. 8,771,314 to Crombie et al., assigned to Ethicon, Inc., discloses a tissue anchor including a body having a longitudinal axis, a proximal end with one set of dimensions and a projected surface area, and a distal end with a second set of dimensions and a projected surface area. The respective dimensions of the first and second ends of the tissue anchor are not identical, however, the projected areas are substantially the same. The tissue anchor has a fixing member to attach the tissue anchor and one or more tissues together.

U.S. Pat. No. 9,198,648 to Crombie et al., assigned to Ethicon, Inc., discloses a wound closure assembly having a curved inserter tool with a distal end and a proximal end, and a filamentary element extending between a proximal end and a distal end, whereby the proximal end is coupled to the proximal end of the curved inserter. A first tissue anchor is coupled to the filamentary element between the first and second ends thereof, and a second tissue anchor is positioned at the distal end of the filamentary element. The filamentary element has a slip knot between the first and second tissue anchors that enables the distance between the first and second tissue anchors to be decreased by pulling on the proximal end of the filamentary element. The distal end of the curved inserter is received within a channel provided in the first tissue anchor, which extends along the length of the first tissue anchor.

In spite of the above-noted advances, there remains a need for improved systems, devices and methods for approximating tissue planes, which minimize seroma formation and that can be performed in a simple, quick, and efficient manner.

In addition, there remains a need for wound closure assemblies that may be implanted by a surgeon using a single hand and using familiar techniques (e.g. using common needle holders), leaving the other hand free to maintain positioning and tension on tissue (e.g., a tissue flap).

There also remains a need for wound closure assemblies that shorten surgical procedures over those that use progressive tissue suturing (PTS) or suture quilting techniques.

SUMMARY OF THE INVENTION

In one embodiment, a wound closure assembly for approximating tissue (e.g., parallel tissue planes) preferably includes a tissue anchor and an insertion tool that is designed to improve the ease of penetration of the tissue anchor and the wound closure assembly through tissue.

In one embodiment, the tissue anchor may be secured to a distal end of the insertion tool, and the distal end of the insertion tool, rather than the leading end of the tissue anchor, functions as the primary tissue penetrating component.

In one embodiment, a wound closure assembly for approximating tissue preferably includes an insertion tool having a proximal end and a distal end with a curved distal section including a penetrating tip at a distal-most end of the insertion tool and first and second notches that are proximal to the penetrating tip and that are formed in respective opposing sides (e.g., first and second lateral sides) of the curved distal section of the insertion tool. In one embodiment, the first and second notches are preferably 180 degrees apart from one another. In one embodiment, the first and second notches are 180 degrees apart from one another on opposite lateral sides of the insertion tool. In one embodiment, the first and second notches may be 180 degrees apart from one another on top and bottom sides of the insertion tool.

In one embodiment, the wound closure assembly preferably includes a tissue anchor having a hollow body with a proximal end, a distal end, an insertion tool channel extending through the hollow body, and first and second spaced tips that project distally from the distal end of the hollow body and that oppose one another on opposite sides of the insertion tool channel. In one embodiment, the first and second spaced tips are preferably flexible to enable the tissue anchor to form a releasable interference fit with the insertion tool.

In one embodiment, in order to secure the tissue anchor to the insertion tool, the curved distal section of the insertion tool is inserted into the insertion tool channel of the tissue anchor so that the penetrating tip of the insertion tool is distal to the first and second spaced tips of the tissue anchor, and so that the first and second spaced tips of the tissue anchor are nested within the respective first and second notches of the insertion tool for generating an interference fit (e.g., a releasable connection) between the first and second spaced tips of the tissue anchor and the curved distal section of the insertion tool.

In one embodiment, the hollow body of the tissue anchor has a curved configuration that matches the curvature of the curved distal section of the insertion tool. The matching curved configurations preferably minimize drag as the insertion tool leads the way for advancing the tissue anchor and the insertion tool through tissue.

In one embodiment, the insertion tool channel of the tissue anchor has a curved configuration that matches the curvature of the curved distal section of the insertion tool.

In one embodiment, the curved distal section of the insertion tool preferably includes the penetrating tip that defines the distal-most end of the insertion tool, the first and second notches that are proximal to the penetrating tip for defining a neck of the curved distal section, and a tissue anchor seating surface that is proximal to the neck and that is adapted to seat the hollow body of the tissue anchor on the curved distal section of the insertion tool.

In one embodiment, the penetrating tip of the insertion tool desirably includes a distal end that defines a distal piercing point and a proximal end of the penetrating tip that is adjacent a distal end of the neck. In one embodiment, the penetrating tip preferably has lateral surfaces that taper outwardly between the distal piercing point and the proximal end of the penetrating tip.

In one embodiment, the neck of the curved distal section of the insertion tool is distal to the tissue anchor seating surface and is proximal to the penetrating tip. In one embodiment, the neck of the curved distal section of the insertion tool preferably has a first laterally extending width, and the proximal end of the penetrating tip has a second laterally extending width that is greater than the first laterally extending width of the neck. In one embodiment, the tissue anchor seating surface of the insertion tool preferably has a third laterally extending width that is greater than the first laterally extending width of the neck.

In one embodiment, the curved distal section of the insertion tool may include a first sloping surface on the first lateral side of the curved distal section that slopes outwardly from the distal end of the neck to the proximal end of the penetrating tip, and a second sloping surface on the second lateral side of the curved distal section that slopes outwardly from the distal end of the neck to the proximal end of the penetrating tip. After the tissue anchor has been advanced into tissue, the sloping surfaces adjacent the proximal end of the penetrating tip preferably facilitate uncoupling of the tissue anchor from the insertion tool as the insertion tool is retracted from tissue. As the insertion tool is retracted, the spaced tips of the tissue anchor may flex outwardly and/or slide over the first and second sloping surfaces that are adjacent the proximal end of the penetrating tip for releasing the tissue anchor from its connection with the curved distal section of the insertion tool.

In one embodiment, the curved distal section of the insertion tool preferably has a cross-sectional dimension having a semicircular shape (e.g., a D-shape) and the insertion tool channel of the tissue anchor has a cross-sectional dimension having a semicircular shape that matches the semicircular shape of the curved distal section of the insertion tool. The matching semicircular shapes enhance the stability of the tissue anchor when it is secured to the curved distal section of the insertion tool (e.g., minimizes twisting and/or shifting of the components relative to one another).

In one embodiment, the distal end of the tissue anchor may have spaced, rounded tips. In one embodiment, the spaced tips have a geometry that blends into tapered geometry of the penetrating tip of the insertion tool. The length of the spaced tips may also vary so that there is a proper fit between the spaced tips of the tissue anchor and the side notches provided on the insertion tool.

In one embodiment, the width of the spaced tips on the tissue anchor may differ from the width of the insertion tool channel of the tissue anchor to ensure a proper interference fit between the tips of the tissue anchor and the side notches of the insertion tool.

In one embodiment, the spaced tips on the tissue anchor have sloping outer surfaces. In one embodiment, when advancing the insertion tool and the tissue anchor through tissue, the sloping outer surfaces on the tips causes the tips to deflect inwardly, thereby facilitating ease of penetration and mitigating potential tissue entrapment between the tissue anchor and the insertion tool.

In one embodiment, the insertion tool channel of the tissue anchor may be modified to allow the insertion tool to pass completely through the tissue anchor. The insertion tool channel may have any geometry that will enable the tissue anchor to properly mate with the insertion tool.

In one embodiment, the geometry at the proximal or trailing end of the tissue anchor may be modified to ensure that the tissue anchor smoothly and consistently disengages from the insertion tool upon retraction of the insertion tool from tissue. In one embodiment, the proximal end of the tissue anchor may have a back wall. The height or thickness of the back wall may vary so that the tissue anchor properly disengages and/or uncouples from the insertion tool. In one embodiment, the back wall at the proximal end of the tissue anchor may be rounded to reduce any potential tissue trauma.

In one embodiment, material may be removed from the bottom of the tissue anchor to reduce the overall profile and/or size of the tissue anchor. The length of the cut that is used to remove the material from the bottom of the tissue anchor, or the area of material that is removed, may vary. In one embodiment, the bottom of the tissue anchor is cut off as only a small portion of the tissue anchor may be needed to releasably secure the tissue anchor to the insertion tool. In one embodiment, the entire bottom of the tissue anchor may be removed, whereby the interference fit between the insertion tool channel and the insertion tool may be used to secure the tissue anchor to the insertion tool.

In one embodiment, the contour of the tissue anchor may be changed from a curved configuration to a straight configuration to match the geometry of a straight insertion tool in order to ensure a proper fit between the tissue anchor and a straight insertion tool.

In one embodiment, the geometry and the positioning of a filamentary element channel may be modified to make the walls of a filamentary element channel more symmetric with respect to the length of the tissue anchor, which preferably increases the tissue anchor's ability to hold tissue. In one embodiment, the length of the tissue anchor on either side of the channel is symmetric and therefore result in similar holding force to surrounding tissue. In one embodiment, the thickness of the tissue anchor surrounding the filamentary element channel or the thickness of the tissue anchor ends proximal or distal to the filamentary element channel may be modified to preferably strengthen the tissue anchors ability to hold tissue.

In one embodiment, the geometry at the distal end of the insertion tool may be modified to have a point to facilitate the penetration of the insertion tool into tissue, similar to the geometry of a suture needle (e.g., an Ethicon CT needle). In one embodiment, the piercing tip geometry may have a taper ratio of anywhere from 1:1 to 12:1, which may be similar to taper ratio range used for taper pointed suture needles that are commercially available.

In one embodiment, the wound closure assembly may also include a filamentary element having a first end secured to the proximal end of the insertion tool and a second end remote from the first end of the filamentary element, whereby the tissue anchor is slidably coupled to the filamentary element between the first and second ends of the filamentary element.

In one embodiment, the wound closure assembly may include a second tissue anchor secured to the filamentary element adjacent the second end of the filamentary element.

In one embodiment, the filamentary element may include a slip knot that is located between the first and second tissue anchors, which enable a distance between the first and second tissue anchors to be decreased by pulling on the first end of the filamentary element via the insertion tool.

In one embodiment, the first and second tissue anchors may be made from a bioabsorbable material, and more preferably a bioabsorbable polymer, such as polydioxanone (PDS), although any suitable biocompatible polymers (absorbable or non-absorbable) may be used.

In one embodiment, the filamentary element may be a suture thread or a monofilament suture, such as a polydioxanone monofilament (e.g., a size-0 polydioxanone monofilament).

In one embodiment, a wound closure assembly preferably includes an insertion tool having a proximal end and a curved distal section, whereby the curved distal section includes a penetrating tip and first and second notches formed in respective first and second lateral sides of the curved distal section.

In one embodiment, the wound closure assembly preferably includes a first tissue anchor having a hollow body with a proximal end, a distal end, and an insertion tool channel extending from the proximal end to the distal end of the hollow body.

In one embodiment, the hollow body of the first tissue anchor preferably includes first and second spaced tips that project distally from the distal end of the hollow body and that oppose one another on opposite sides of the insertion tool channel. The first and second spaced tips may be flexible for flexing toward and away from one another. The first and second spaced tips may have free, distal ends that define convexly curved surfaces.

In one embodiment, the curved distal section of the insertion tool is desirably inserted into the insertion tool channel of the first tissue anchor so that the penetrating tip is distal to the first and second spaced tips (i.e., extends distal to the distal end of the first tissue anchor) and the first and second spaced tips are seated within the respective first and second notches formed in the sides of the insertion tool for generating an interference fit between the first and second spaced tips of the first tissue anchor and the curved distal section of the insertion tool.

In one embodiment, the wound closure assembly desirably includes a filamentary element having a first end secured to the proximal end of the insertion tool and a second end remote from the first end. In one embodiment, the wound closure assembly desirably includes a second tissue anchor secured to the filamentary element adjacent the second end of the filamentary element.

In one embodiment, the filamentary element desirably includes a slip knot that is located between the first and second tissue anchors for enabling a distance between the first and second tissue anchors to be decreased by pulling on the first end of the filamentary element that is attached to the proximal end of the insertion tool.

In one embodiment, the insertion tool channel of the hollow body of the first tissue anchor preferably has a curved configuration that matches the curvature of the curved distal section of the insertion tool.

In one embodiment, the curved distal section of the insertion tool preferably includes the penetrating tip that defines a distal-most end of the insertion tool, the first and second notches that are proximal to the penetrating tip for defining a neck of the curved distal section, and a first tissue anchor seating surface that is proximal to the first and second notches and that is adapted to seat the hollow body of the first tissue anchor.

In one embodiment, the penetrating tip of the insertion tool preferably includes a distal end that defines a distal piercing point at a distal-most end of the insertion tool and a proximal end that is connected to a distal end of the neck. In one embodiment, the penetrating tip desirably has lateral surfaces that taper outwardly from the distal piercing point to the proximal end of the penetrating tip.

In one embodiment, the neck of the curved distal section of the insertion tool preferably has a first laterally extending width and the proximal end of the penetrating tip has a second laterally extending width that is greater than the first laterally extending width of the neck. As a result, when the first tissue anchor is secured to the curved distal section of the insertion tool, the spaced tips of the first tissue anchor are nested within the respective first and second notches of the insertion tool, and the lateral surfaces of the penetrating tip cover the spaced tips of the first tissue anchor as the first tissue anchor is advanced into tissue.

In one embodiment, the insertion tool has a first sloping surface on the first lateral side of the curved distal section that slopes outwardly from the distal end of the neck to the proximal end of the penetrating tip, and a second sloping surface on the second lateral side of the curved distal section that slopes outwardly from the distal end of the neck to the proximal end of the penetrating tip. The first and second sloping surfaces face toward a proximal end of the first tissue anchor seating surface and face away from the piercing point located at the distal end of the penetrating tip of the insertion tool. In one embodiment, the first and second spaced tips of the first tissue anchor are shrouded by the first and second sloping surfaces that extend from the distal end of the neck to the proximal end of the penetrating tip.

In one embodiment, the curved distal section of the insertion tool has a cross-sectional dimension with a semicircular shape and the insertion tool channel of the first tissue anchor has a cross-sectional dimension with a semicircular shape that matches the semicircular shape of the curved distal section of the insertion tool.

In one embodiment, the insertion tool preferably includes a stop (e.g., a vertical wall) that is located at a proximal end of the first tissue anchor seating surface, which is adapted to engage the proximal end of the hollow body of the first tissue anchor to halt movement of the hollow body toward the proximal end of the insertion tool.

In one embodiment, the insertion tool channel extending through the first tissue anchor preferably defines a first lateral width, and the first and second spaced tips of the first tissue anchor have opposing inner surfaces that define a second lateral width that is smaller than the first lateral width of the insertion tool channel. The first lateral width of the insertion tool channel accommodates the laterally extending width of the tissue anchor seating surface of the insertion tool and the smaller second lateral width defined by the first and second spaced tips ensures that the spaced tips will nest within the notches of the insertion tool.

In one embodiment, a kit may include a plurality of wound closure assemblies contained within a single package. The wound closure assemblies may be similar in construction to those disclosed in the present patent application.

In one embodiment, each wound closure assembly in a kit may include an insertion tool having a proximal end and a curved distal section including a penetrating tip at a distal-most end of the insertion tool, and first and second notches that are proximal to the penetrating tip and that are formed in respective first and second lateral sides of the curved distal section.

In one embodiment, each wound closure assembly in a kit may also include a tissue anchor having a hollow body with a proximal end, a distal end, an insertion tool channel extending through the hollow body, and first and second spaced tips that project distally from the distal end of the hollow body and that oppose one another on opposite sides of the insertion tool channel.

In one embodiment, for each wound closure assembly of the kit, the curved distal section of the insertion tool is preferably insertable into the insertion tool channel of the tissue anchor so that the penetrating tip is distal to the first and second spaced tips, and the first and second spaced tips are nested within the respective first and second notches of the insertion tool for generating an interference fit between the first and second spaced tips of the tissue anchor and the curved distal section of the insertion tool.

In one embodiment, each wound closure assembly of the kit may also include a filamentary element having a first end secured to the proximal end of the insertion tool and a second end remote from the first end, whereby the tissue anchor is slidably coupled to the filamentary element between the first and second ends of the filamentary element.

In one embodiment, each wound closure assembly of the kit may also include a second tissue anchor secured to the second end of the filamentary element. The filamentary element may include a slip knot that is located between the first and second tissue anchors, which enable a distance between the first and second tissue anchors to be decreased by pulling on the first end of the filamentary element via the insertion tool.

In one embodiment, an insertion tool desirably includes a stop or vertical wall that prevents the tissue anchor from sliding back along the body of the insertion tool (e.g., toward the proximal end of the insertion tool). The height of the vertical wall may vary and the insertion tool may also have an angled ramped to transition back to the elongated body of the insertion tool. The angled ramp may have any angle such that it allows for the filamentary element (e.g., a suture loop) of the wound closure assembly to freely pass through the filamentary element channel of the tissue anchor. The height of the vertical wall may also be designed so that there is no angled ramp to transition to the elongated body of the insertion tool and there is only a direct transition from the vertical wall to the elongated body.

In one embodiment, notches are located on both sides of the insertion tool to allow for a secure fit of the tissue anchor, specifically the spaced, rounded tips of the tissue anchor. The length of the notches may vary. The notches may extend the entire length from the notch point of the insertion tool to the vertical wall, or only a partial length. The width of the notches may also vary in order to provide a secure, interference fit between the tissue anchor and the insertion tool. The interference fit between the notches and the spaced, rounded tips preferably allows for controlled release of the tissue anchor from the insertion tool.

In one embodiment, the insertion tool has a curved distal section that reduces the drag of the wound closure assembly while passing the tissue anchors and the insertion tool through tissue. In one embodiment, the cross-sectional shape of the distal end of the insertion tool has a D-shape whereby the top of the circular profile is eliminated to create a D-profile. In other embodiments, however, the distal end of the insertion tool may have a square, rectangular, trapezoidal, or any other body shape that facilitates a proper fit between the insertion tool and the tissue anchor, which preferably has a matching receiving shape.

In one embodiment, the length of the curved distal section of the insertion tool is increased to allow the insertion tool to completely pass through the tissue anchor so that the insertion tool penetrates through tissue. The length of the curved distal section may vary so long as the insertion tool is able to pass through the tissue anchor and the distal tip of the insertion tool is exposed to penetrate through tissue.

In one embodiment, the distal end of the first tissue anchor has a pair of rounded tips that are spaced from one another, with the inner channel of the first tissue anchor passing between the spaced tips. In one embodiment, the rounded tips have sloping outer surfaces that are designed to match (i.e., blend) with the taper of the insertion tool so that there is no discernible step from the insertion tool to the first tissue anchor at the transition point between the two components.

These and other preferred embodiments of the present patent application will be described in more detail below.

BRIEF DESCRIPTION OF THE DRAWINGS

FIG. 48 is a side view of the second tissue anchor shown in FIG. 4A.

FIG. 9F-1 is a cross-sectional view of the first tissue anchor and the distal end of the insertion tool taken along line 9F-1-9F-1 of FIG. 9D.

FIG. 9F-2 is a magnified view of the cross-section of the first tissue anchor and the insertion tool shown in FIG. 9F-1.

DETAILED DESCRIPTION OF PREFERRED EMBODIMENTS

Figure 1:
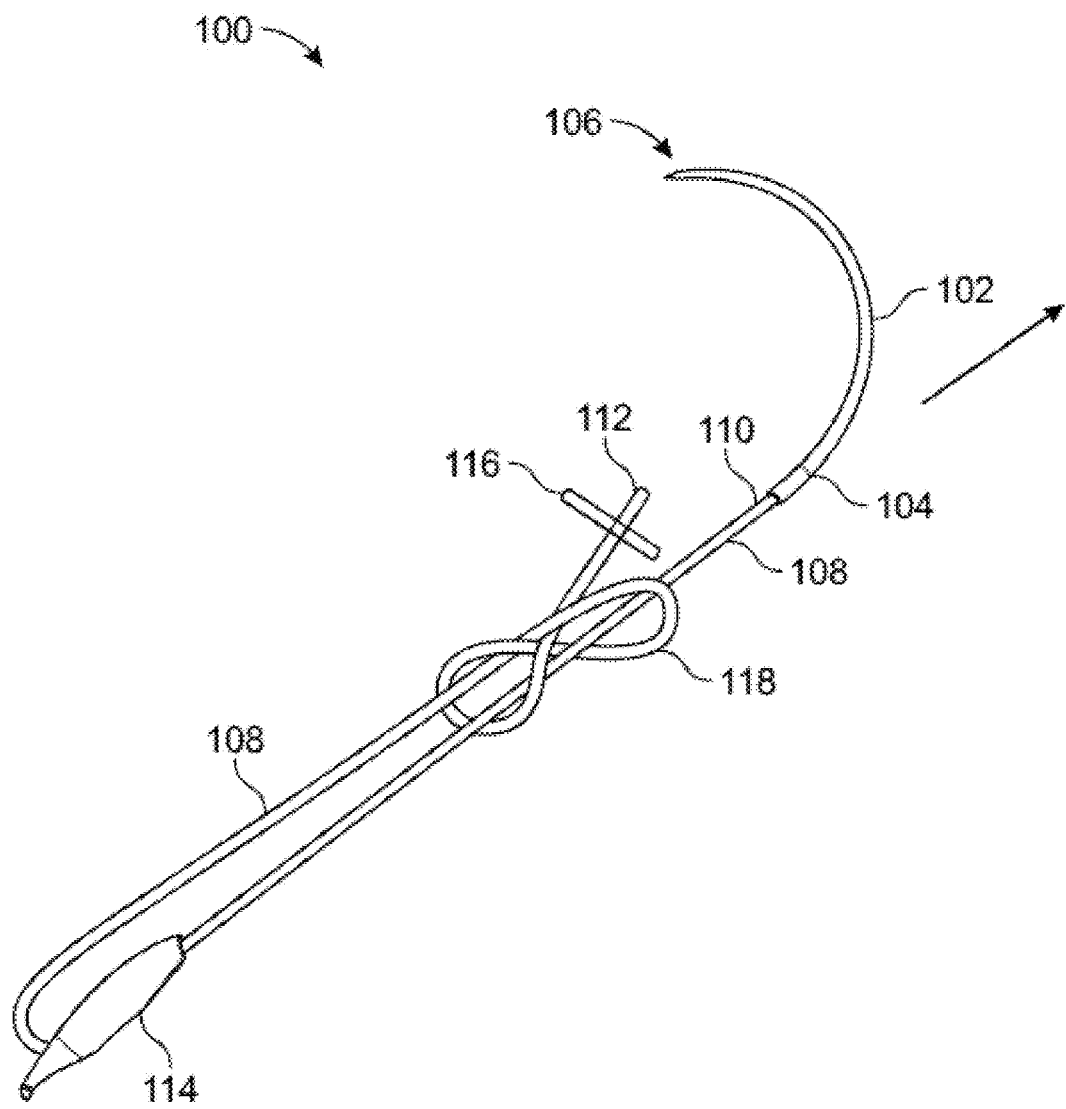
FIG. 1 is a schematic view of a wound closure assembly used for tissue approximation including a first tissue anchor, a second tissue anchor, a filamentary element, a fixation knot, a slip knot, and an insertion tool, in accordance with one embodiment of the present patent application.

Referring to FIG. 1, in one embodiment, a wound closure assembly 100 for approximating tissue (e.g., two tissue planes) preferably includes a curved insertion tool 102 having a proximal end 104 and a distal end 106. In one embodiment, the curved insertion tool 102 may have one or more features that are similar to those found in a standard surgical needle (e.g., made of stainless steel), which is used for suturing tissue.

In one embodiment, the wound closure assembly 100 preferably includes a filamentary element 108 (e.g., a monofilament suture) that is secured to the proximal end 104 of the insertion tool 102. In one embodiment, the filamentary element 108 preferably has a first end 110 that is secured to the proximal end 104 of the insertion tool 102 and a second end 112 that is remote from the first end 110 of the filamentary element, In one embodiment, the wound closure assembly 100 preferably includes a first tissue anchor 114 and a second tissue anchor 116 that are coupled to the filamentary element 108. In one embodiment, the first and second tissue anchors 114, 116 are designed and configured for being implanted in tissue. In one embodiment, the first tissue anchor 114 is slidably coupled to the filamentary element 108 so that the first tissue anchor 114 is free to slide along the length of the filamentary element, preferably by passing the filamentary element through a filamentary element channel of the first tissue anchor, as will be described in more detail herein. In one embodiment, the second tissue anchor 116 is preferably secured adjacent a second end 112 of the filamentary element 108. In one embodiment, the second tissue anchor 116 is fixedly secured to the second end of the filamentary element using a fixed knot.

In one embodiment, the filamentary element 108 of the wound closure assembly preferably has a slip knot 118 formed therein that is located between the first end 110 and the second end 112 of the filamentary element. As used herein, the term "slip knot" is defined to mean a knot that can slip along the length of the filamentary element 108 by pulling one end of the filamentary element. Preferably, the slip knot 118 is positioned between the first tissue anchor 114 and the second tissue anchor 116 so as to enable the distance between the first and second tissue anchors 114, 116 to be reduced by pulling on the first end 110 of the filamentary element 108 (e.g., by using the insertion tool 102 to pull the first end 110 of the filamentary element 108) as shown by the arrow in FIG. 1. In this manner, tight approximation of tissue layers may be achieved.

Referring to FIGS. 2A-2F, in one embodiment, the first tissue anchor 114 preferably includes a hollow body 120 having a proximal end 122, a distal end 124, and an insertion tool channel 126 that extends from the proximal end 122 to the distal end 124 of the hollow body. In one embodiment, the hollow body 120 has a length and the insertion tool channel 126 extends along the length of the hollow body. In one embodiment, the insertion tool channel 126 is configured to receive the distal end 106 of the insertion tool 102 (FIG. 1) for releasably securing the first tissue anchor to the distal end of the insertion tool. In one embodiment, the hollow body 120 preferably has a curved configuration that is designed to match the curved configuration of the distal end of the insertion tool 102 (FIG. 1), as will be described in more detail herein. In one embodiment, the hollow body 120 of the first tissue anchor 114 has a top side 128 having a concave surface and a bottom side 130 having a convexly curved surface that preferably matches the curvature of the distal end of the insertion tool.

In one embodiment, the proximal end 122 of the hollow body 120 of the first tissue anchor 114 desirably has a back wall 132 that projects proximally from an underside of the hollow body 120. In one embodiment, the distal end 124 of the hollow body 120 preferably includes a pair of spaced tips 134A, 134B that are adapted to engage lateral notches formed in the sides of the distal end of the insertion tool, as will be described in more detail herein.

In one embodiment, the distal ends of the respective spaced tips 134A, 134B are preferably rounded. In one embodiment, the spaced tips 134A, 134B are made of a flexible material so that the tips may flex away from one another when initially securing the first tissue anchor 114 to the distal end 106 of the insertion tool 102 (e.g., prior to insertion into tissue) and flex away from one another when uncoupling the first tissue anchor from the distal end of the insertion tool, such as after the first tissue anchor has been inserted into tissue and during retraction of the distal end of the insertion tool from the tissue. In one embodiment, the spaced tips 134A, 134B are preferably flexible for forming an interference fit with the lateral notches that are formed in the sides of the distal end of the insertion tool, which enables the first tissue anchor 114 to be releasably secured to the distal end of the insertion tool. In one embodiment, the spaced tips 134A, 134B are preferably flexible and have sloping outer surfaces, which enables the tips to deflect inwardly during penetration and mitigating potential tissue drag and tissue entrapment between the tissue anchor and the insertion tool.

Referring to FIG. 2O, in one embodiment, the insertion tool channel 126 preferably extends along the length of the hollow body 120 of the first tissue anchor 114. In one embodiment, the insertion tool channel 126 preferably extends between the back wall 132 located at the proximal end 122 of the hollow body 120 and the distal ends of the spaced tips 134A, 134B located at the distal end 124 of the hollow body 120. In one embodiment, the hollow body 120 has a mid-section 136 that defines an outer diameter $D_1$ of the hollow body, and the spacing between the tips 134A, 134B defines a distance $D_2$ that is less than the outer diameter distance $D_1$. In one embodiment, each spaced tip 134A, 134B has a respective outer surface 138A, 138B that slopes or tapers inwardly between the larger outer diameter $D_1$ of the hollow body 120 and the smaller distance $D_2$ between the spaced tips 134A, 134B.

In one embodiment, the mid-section 136 of the hollow body 120 is preferably closed at the topside of the elongated body 120 to define a filamentary element channel 127 that extends along the length of the hollow body and that is located above the upper end of the insertion tool channel 126. The filamentary element channel 127 preferably enables a loop of the filamentary element 108 (FIG. 1) to pass through the proximal and distal ends of the filamentary element channel 127 for connecting the first tissue anchor 114 to the filamentary element 108 (FIG. 1).

Figure 2A:
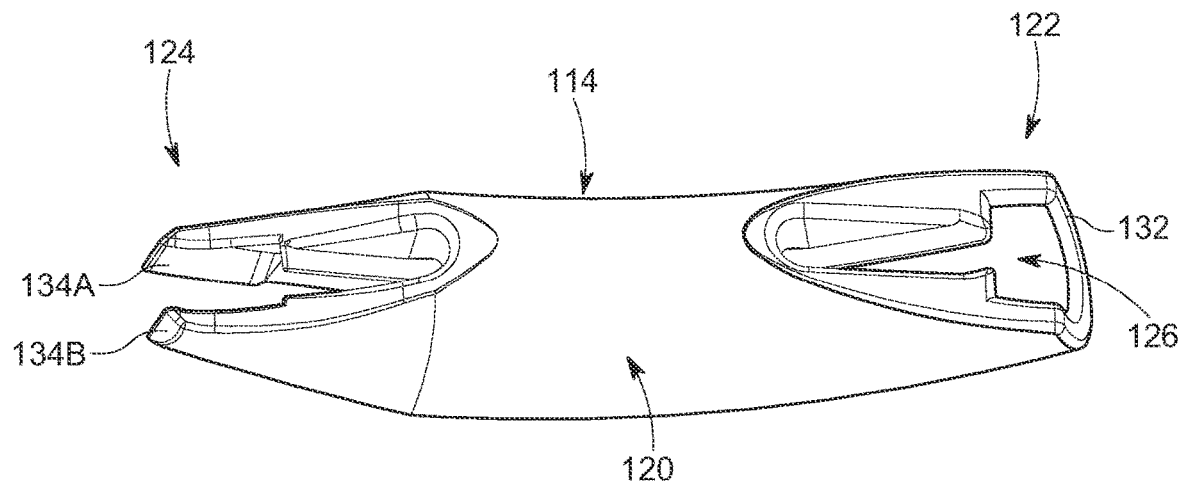
FIG. 2A is a perspective view of a first tissue anchor for a wound closure assembly, in accordance with one embodiment of the present patent application.
Figure 2B:
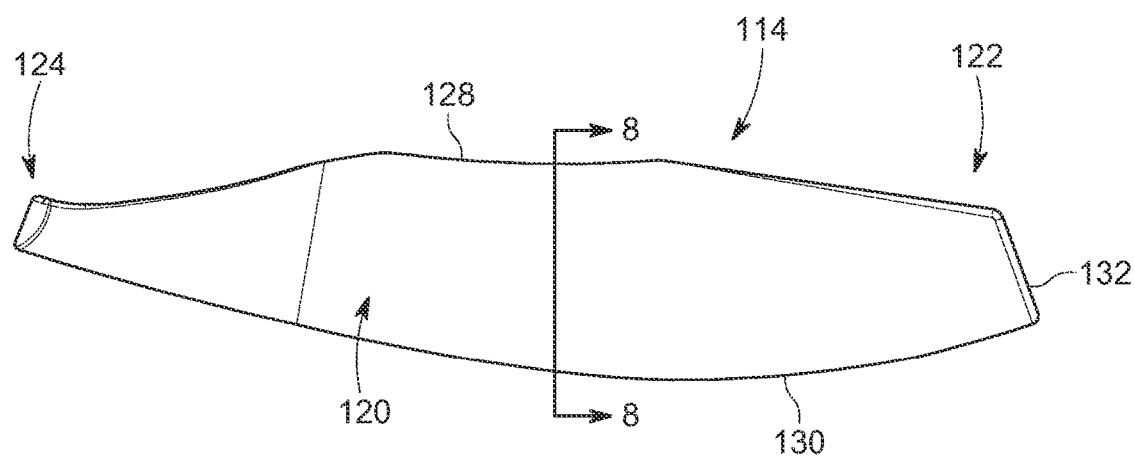
FIG. 2B is a side view of the first tissue anchor shown in FIG. 2A.
Figure 2C:
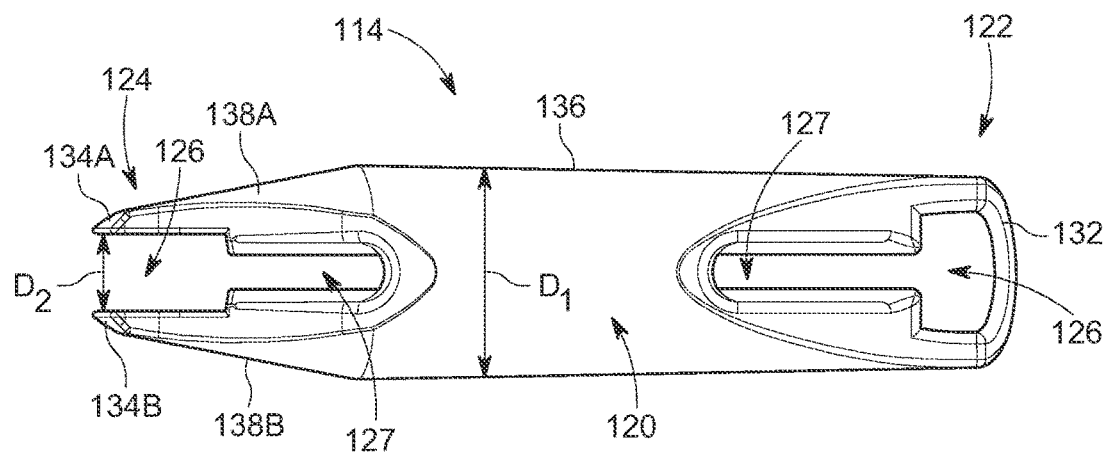
FIG. 2C is a top view of the first tissue anchor shown in FIGS. 2A and 28.
Figure 2D:
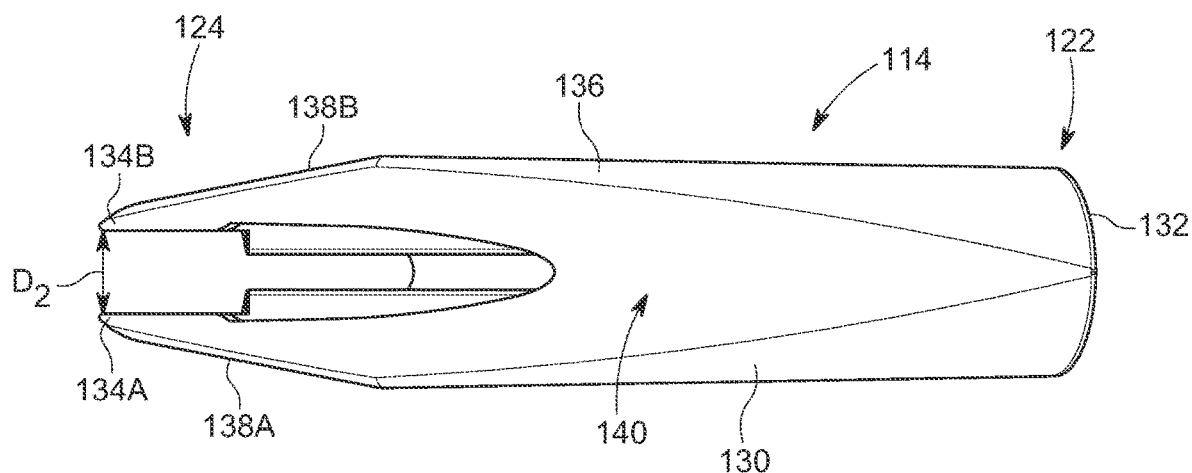
FIG. 2D is a bottom view of the first tissue anchor shown in FIGS. 2A-2C.

Referring to FIGS. 2B and 2D, in one embodiment, the first tissue anchor 114 preferably has the bottom surface 130. In one embodiment, a section of the bottom surface 130 of the first tissue anchor is partially removed to reduce the overall profile, size and/or dimension of the first tissue anchor. In one embodiment, the partially removed material from the bottom surface 130 of the first tissue anchor 114 may include a tapered surface 140. The length, size, area, and/or dimension of the cut 140 that is formed in the bottom surface 130 of the first tissue anchor 114 may vary.

Figure 2E:
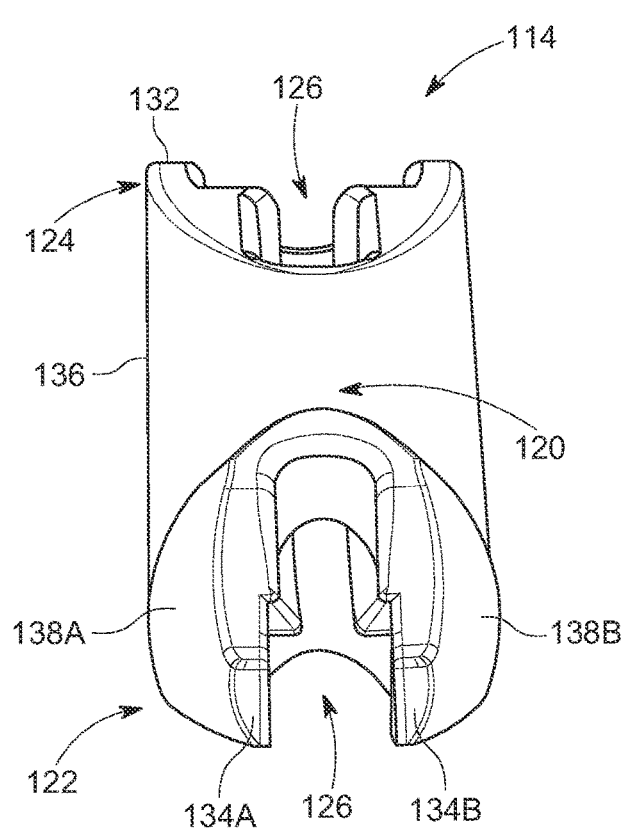
FIG. 2E is a perspective view of a distal end of the first tissue anchor shown in FIGS. 2A-2D.
Figure 2F:
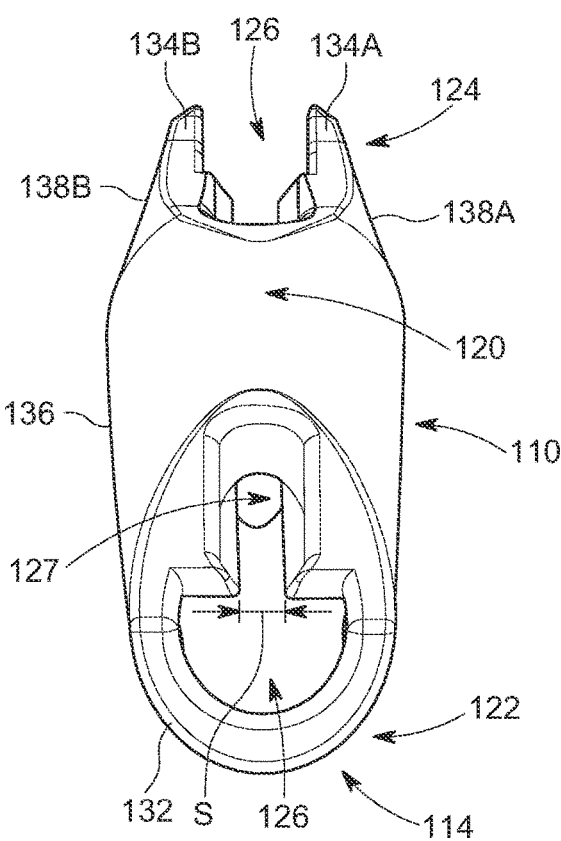
FIG. 2F is a perspective view of a proximal end of the first tissue anchor shown in FIGS. 2A-2E.

Referring to FIGS. 2E and 2F, in one embodiment, the filamentary element channel 127 preferably extends along the length of the hollow body 120 of the first tissue anchor 114. In one embodiment, the filamentary element channel 127 is preferably located above the upper end of the insertion tool channel 126. In one embodiment, the filamentary element preferably passes through the filamentary element channel for slidably coupling the first tissue anchor with the filamentary element. In one embodiment, the filamentary element channel 127 may be open to the insertion tool channel 126 to further reduce the overall profile of the anchor, with the opening dimensioned such that the filamentary element 108 cannot inadvertently enter the insertion tool channel. In one embodiment, the spacing S (FIG. 2F) between the opposing side walls of the filamentary element channel 127 is less than the diameter of a filament (e.g., a suture thread) to keep the filament captured within the filamentary element channel 127 and prevent the filament from moving into the insertion tool channel 126 of the hollow body 120.

In one embodiment, the spaced tips 134A, 134B of the first tissue anchor 114 are preferably located at the distal end 124 of the hollow body 120, and the back wall 132 is preferably located at the proximal end 126 of the hollow body 120. The spaced tips 134A, 134B have respective inwardly sloping outer surfaces 138A, 138B that slope inwardly between the wider mid-section 136 of the hollow body 120 and the narrower distal-most ends of the spaced tips 134A, 134B. The first tissue anchor 114 is coupled with a filamentary element by passing the filamentary element through the proximal and distal sections of the filamentary element channel 127, and wrapping the filamentary element around the mid-section 136 of the hollow body 120 for capturing the hollow body within a closed end and/or loop of the filamentary element.

Figure 3A:
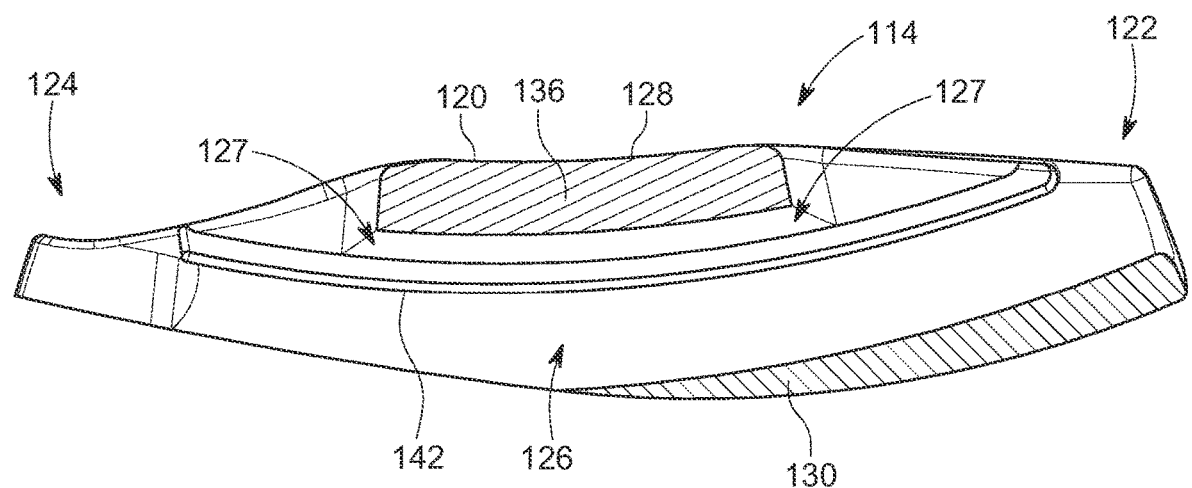
FIG. 3A is a cross-sectional side view of the first tissue anchor shown in FIGS. 2A-2F thereof.

Referring to FIG. 3A, in one embodiment, the hollow body 120 of the first tissue anchor 114 preferably has a generally curved configuration including a concave top surface 128 and a convexly curved bottom surface 130 that are adapted to generally match the curvature of the distal end (e.g., the curved distal section) of the insertion tool 102 (FIG. 1). In one embodiment, the first tissue anchor 114 preferably includes the insertion tool channel 126 that extends from the proximal end 122 to the distal end 124 of the hollow body 120. The insertion tool channel 126 is preferably curved to match the curvature of the distal end of the insertion tool. The hollow body 120 of the first tissue anchor 114 preferably includes the filamentary element channel 127 that extends between the insertion tool channel 126 and the concave top surface 128 of the hollow body 120.

In one embodiment, the insertion tool channel 126 is curved and has an insertion tool guide surface 142 that is located at the upper end of the insertion tool channel 126. In one embodiment, the insertion tool guide surface 142 is preferably curved to match the curvature of the distal end of the insertion tool. In one embodiment, when the distal end of the insertion tool is inserted into the insertion tool channel 126, the top surface of the distal end of the insertion tool preferably slides over the insertion tool guide surface 142.

In one embodiment, the hollow body 120 of the first tissue anchor 114 preferably has the mid-section 136 that is closed so that a closed end of a filamentary element may be passed through the filamentary element channel 127 and wrapped around the mid-section 136 of the elongated body 120 for coupling the first tissue anchor 114 with the closed end of the filamentary element. In one embodiment, the first tissue anchor is free to slide relative to the filamentary element.

Figure 3B:
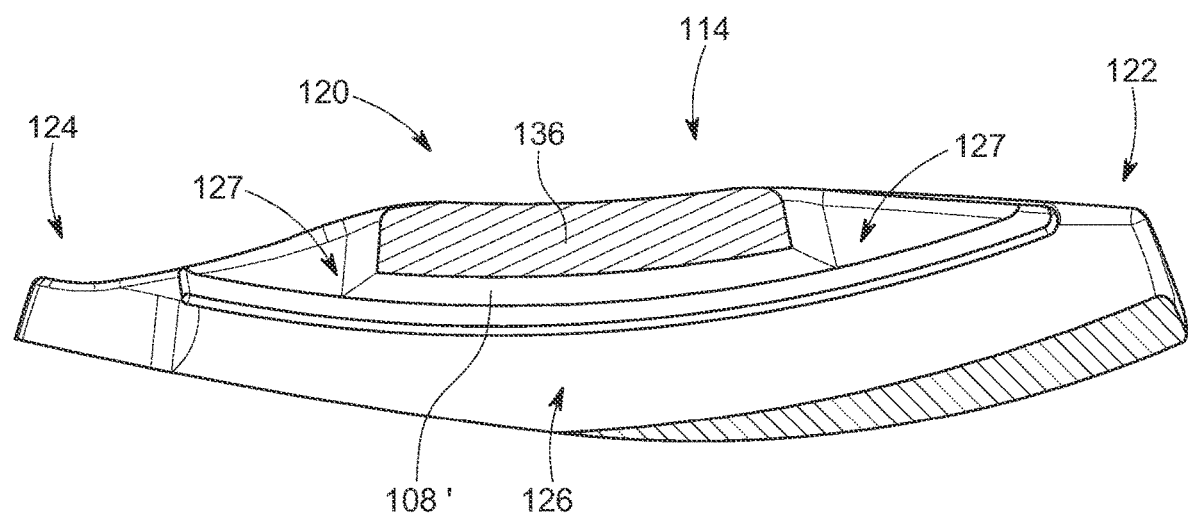
FIG. 3B is the cross-sectional side view of the first tissue anchor of FIG. 3A with a filamentary element passing through a filamentary element channel of the first tissue anchor.

Referring to FIG. 3B, in one embodiment, the closed end of a filamentary element 108 (FIG. 1) may be passed through the filamentary element channel 127 and wrapped around the closed mid-section 136 of the hollow body 120 for coupling the first tissue anchor 114 with the filamentary element, whereupon the first tissue anchor 114 is able to slide and/or toggle relative to the closed end of the filamentary element, which facilitates properly anchoring the first tissue layer within tissue and approximating two tissue layers together during a surgical procedure, as will be described in more detail herein. In one embodiment, the closed mid-section 136 is centered along the length of the hollow body 120 so that it is equidistant between the proximal and distal ends 122, 124 of the hollow body 120.

Figure 4A:
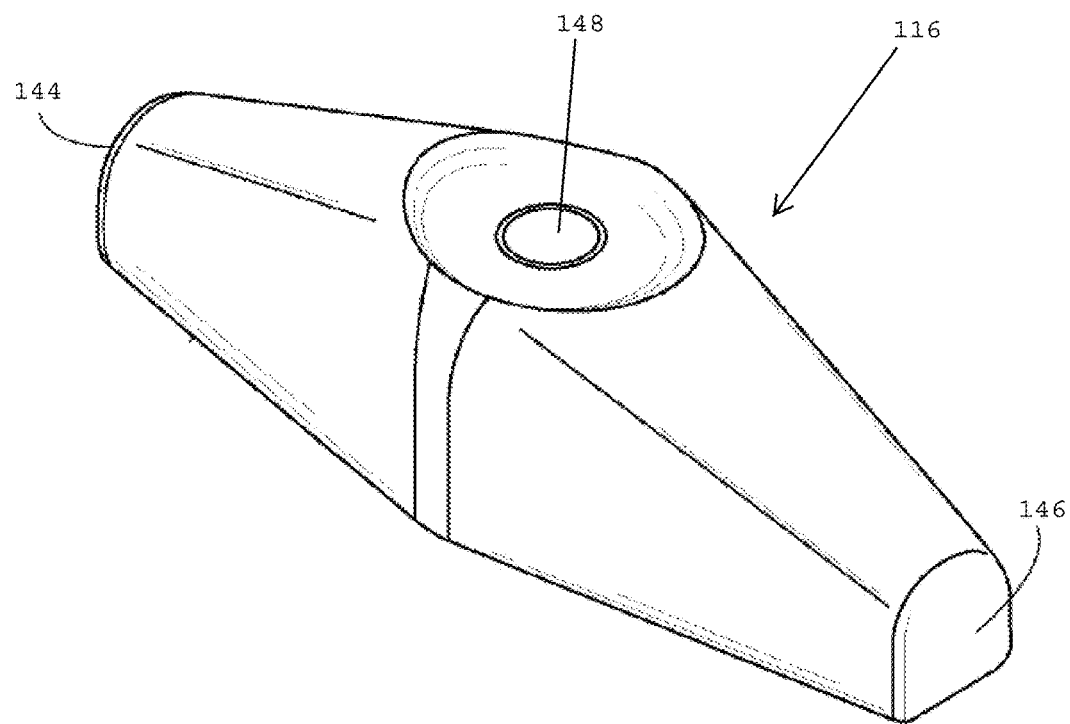
FIG. 4A is a perspective view of a second tissue anchor of a wound closure assembly, in accordance with one embodiment of the present patent application.
Figure 4B:
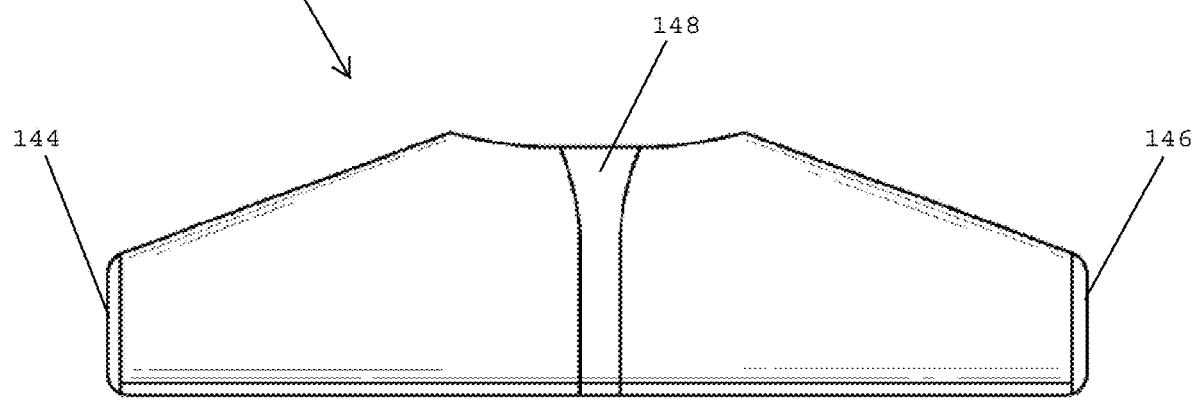

Referring to FIGS. 4A and 4B, in one embodiment, the second tissue anchor 116 (FIG. 1) preferably includes blunt first and second ends 144, 146 and a central opening 148 that is adapted to receive the second end 112 of the filamentary element 108 (FIG. 1). In one embodiment, after the second end of the filamentary element is passed through the central opening 148 of the second tissue anchor 116, a fixed knot may be formed at the second end 112 of the filamentary element 108 (FIG. 1) for fixedly securing the second tissue anchor to the second end of the filamentary element.

In one embodiment, the second tissue anchor 116 may be a separate element secured to the second end of the filamentary element. In one embodiment, however, the second tissue anchor may be integrally formed with the second end of the filamentary element, such as by braiding or otherwise winding the second end of the filamentary element to form an enlarged stop. In one embodiment, the second tissue anchor may be made of a material other than a solid biocompatible polymer, such as a mesh element having a disc or plate-like shape, whereby the mesh element preferably promotes tissue in-growth.

Figure 5A:
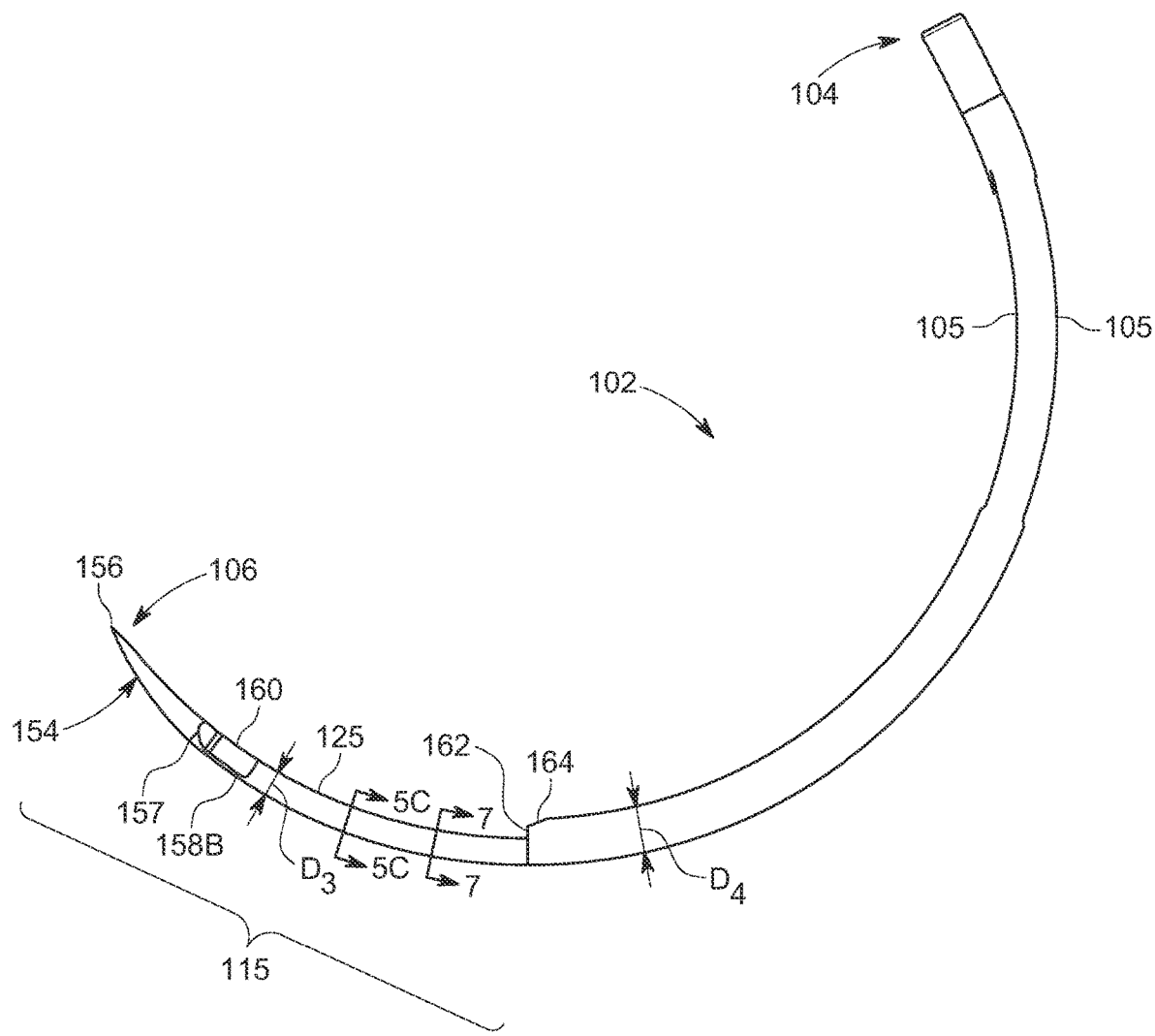
FIG. 5A is a side view of an insertion tool of a wound closure assembly, in accordance with one embodiment of the present patent application
Figure 5B:
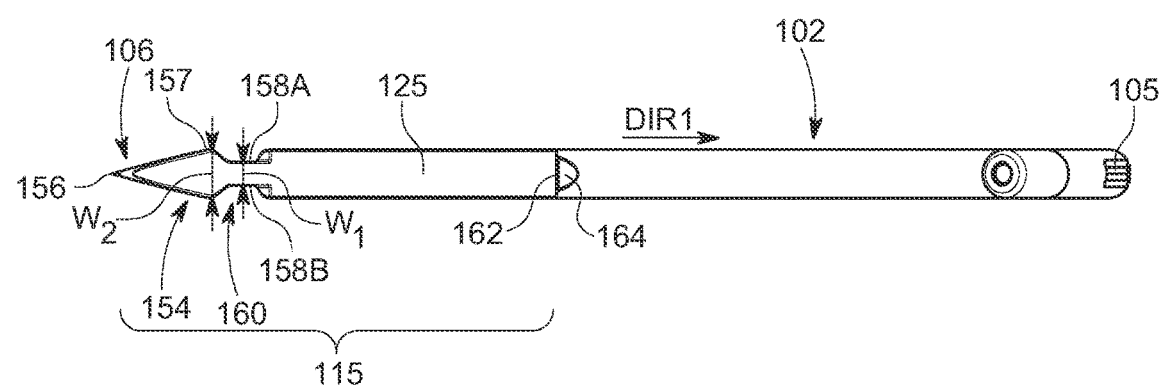
FIG. 5B is a top view of the insertion tool shown in FIG. 5A.

Referring to FIGS. 5A and 5B, in one embodiment, the insertion tool 102 preferably includes an elongated body that is curved between the proximal end 104 and the distal end 106 thereof. In one embodiment, the insertion tool 102 has curved shape that is generally similar to that found in a curved suture needle. In one embodiment, the insertion tool 102 preferably includes ribs 105 (e.g., longitudinally extending ribs) formed in an outer surface of the elongated body as disclosed in U.S. Pat. No. 3,160,157 to Chisman, assigned to Ethicon, Inc., the disclosure of which is hereby incorporated by reference herein. In one embodiment, the insertion tool 102 preferably has a curved distal section 115 that extends to the distal end 106 of the insertion tool. The curved distal section 115 preferably has a thickness or diameter $D_3$ that is smaller than the thickness or diameter $D_4$ of the portion of the elongated body that extends between the curved distal section 115 and the proximal end 104 of the insertion tool 102.

In one embodiment, the curved distal section 115 of the insertion tool 102 preferably includes a penetrating tip 154 having a distal-most end with a distal point 156 and a proximal end 157. The penetrating tip 154 preferably tapers outwardly from the distal point 156 to the proximal end 157 of the penetrating tip.

In one embodiment, the curved distal section 115 of the insertion tool 102 preferably includes first and second notches 158A, 158B that are formed in the respective lateral sides of the curved distal section 115, which define a neck region 160 of the curved distal section 115 that has a first width $W_1$ that is smaller than the second width $W_2$ at the proximal end 157 of the penetrating tip 154.

In one embodiment, the curved distal section 115 of the insertion tool 102 preferably includes a first tissue anchor seating section 125 that extends between the neck 160 and a stop or vertical wall 162 that is located at a proximal end of the first tissue anchor seating section 125. In one embodiment, the vertical wall 162 functions as a hard stop that is adapted to engage the proximal end of the first tissue anchor 114 (FIG. 2A) for preventing the first tissue anchor from sliding back in a proximal direction DIR1 (FIG. 5B) on the curved body of the insertion tool 102. In one embodiment, the insertion tool 102 includes a sloping surface 164 that is proximal to the vertical wall 162, which preferably enables the filamentary element 108 (FIG. 3B) that is coupled with the first tissue anchor to pass between the first tissue anchor and the curved body of the insertion tool 102.

Figure 5C:
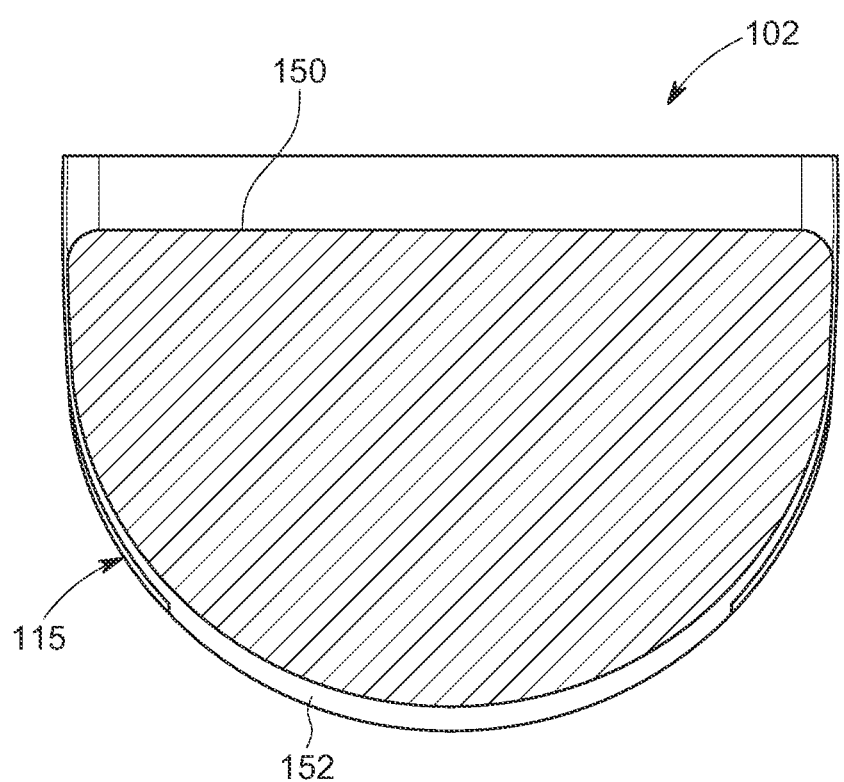
FIG. 5C is a cross-sectional view of a distal end of the insertion tool of FIGS. 5A and 5B taken along line 5C-5C of FIG. 5A.

Referring to FIG. 5C, in one embodiment, the curved distal section 115 of the insertion tool 102 (FIG. 5A) desirably has a cross-section having a generally semicircular shape. In one embodiment, the semicircular shaped cross-section of the curved distal section 115 of the insertion tool preferably includes a flat top surface 150 and a convexly-curved underside 152. In one embodiment, the cross-sectional shape of the distal end of the insertion tool may also have an appearance that is similar to the capital letter D.

Figure 5D:
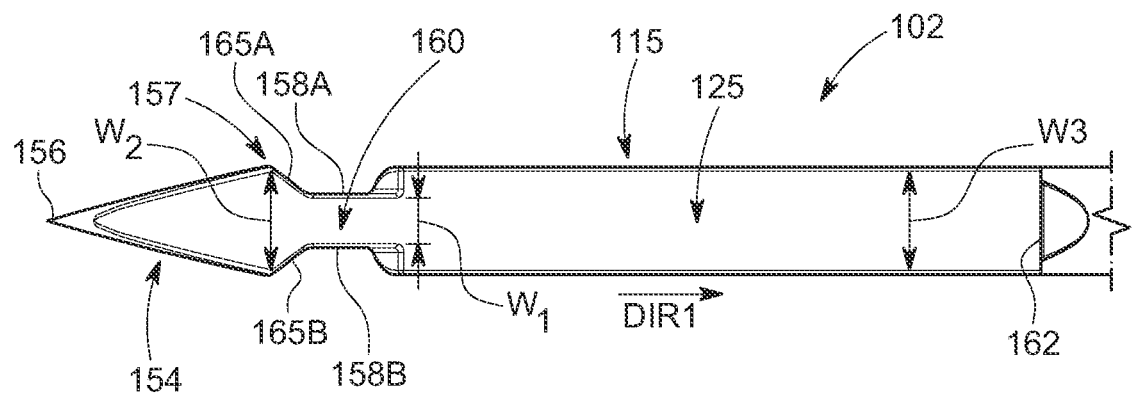
FIG. 5D is a top view of the distal end of the insertion tool shown in FIGS. 5A-5C.
Figure 5E:
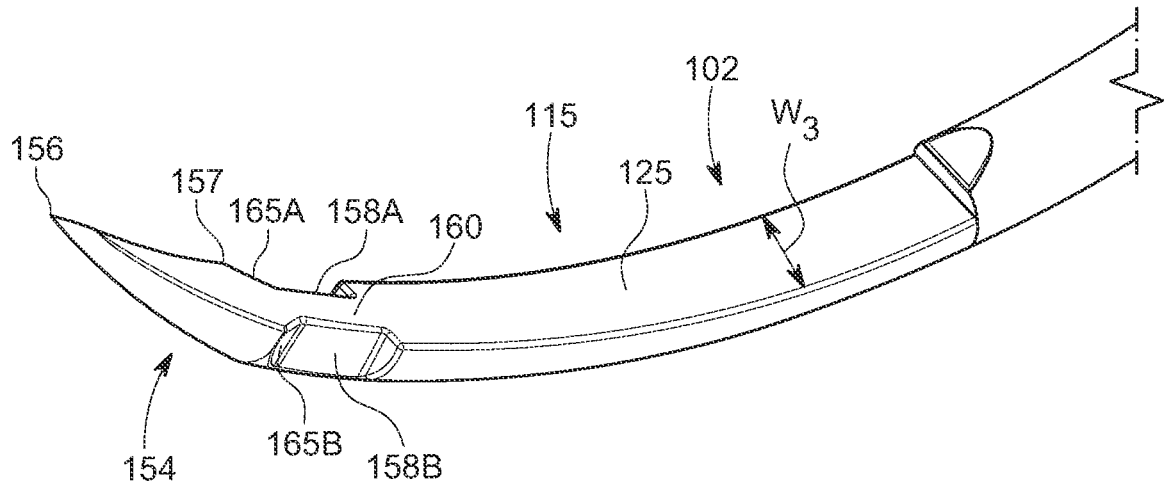
FIG. 5E is a perspective view of the distal end of the insertion tool shown in FIGS. 5A-5D.
Figure 5F:
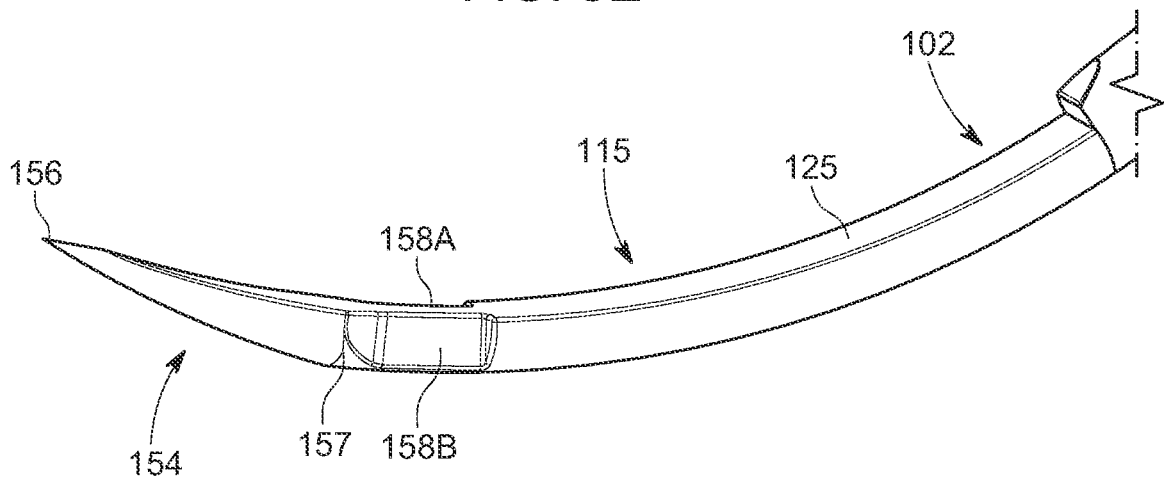
FIG. 5F is a side view of the distal end of the insertion tool shown in FIGS. 5A-5E.

Referring to FIGS. 5D-5F, in one embodiment, the curved distal section 115 of the insertion tool 102 preferably includes the first and second lateral notches 158A, 158B that define the neck 160, which has a smaller width $W_1$ than the larger width $W_2$ at the proximal end 157 of the penetrating tip 154. Thus, the first width $W_1$ of the neck 160 of the insertion tool is smaller than the second width $W_2$ at the proximal end 157 of the penetrating tip 154. In addition, the first width $W_1$ of the neck is smaller than the third width $W_3$ of the anchor seating section 125 of the insertion tool. In one embodiment, the second width $W_2$ of the proximal end 157 of the penetrating tip 154 and the third width $W_3$ of the first tissue anchor seating surface 125 may match one another.

Referring to FIG. 5D, in one embodiment, the penetrating tip 154 tapers outwardly from the distal point 156 to the proximal end 157 of the penetrating tip. In one embodiment, the taper ratio may be between 1:1 and 12:1. In one embodiment, the curved distal section 115 of the insertion tool tapers outwardly between the narrower first width $W_1$ of the neck 160 and the wider second width W₂ at the proximal end 157 of the penetrating tip 154 to define respective first and second sloping surfaces 165A, 165B that are adapted to engage the spaced tips 134A, 134B of the first tissue anchor 114 (FIG. 2A). The first and second sloping surfaces 165A, 165B preferably face in a proximal direction DIR1.

Referring to FIGS. 5D-5F, in one embodiment, the first sloping surface 165A is associated with the first notch 158A and extends outwardly between the distal end of the neck 160 and the proximal end 157 of the penetrating tip 154, and the second sloping surface 165B is associated with the second notch 158B and extends outwardly between the distal end of the neck 160 and the proximal end 157 of the penetrating tip 154. When the insertion tool 102 is retracted from tissue, the first and second sloping surfaces 165A and 165B preferably facilitate release of the first tissue anchor from the curved distal section 115 of the insertion tool. In one embodiment, as the insertion tool is retracted, the spaced tips of the tissue anchor flex outwardly from one another as they slide over the respective first and second sloping surfaces 165A, 165B.

Figure 6A:
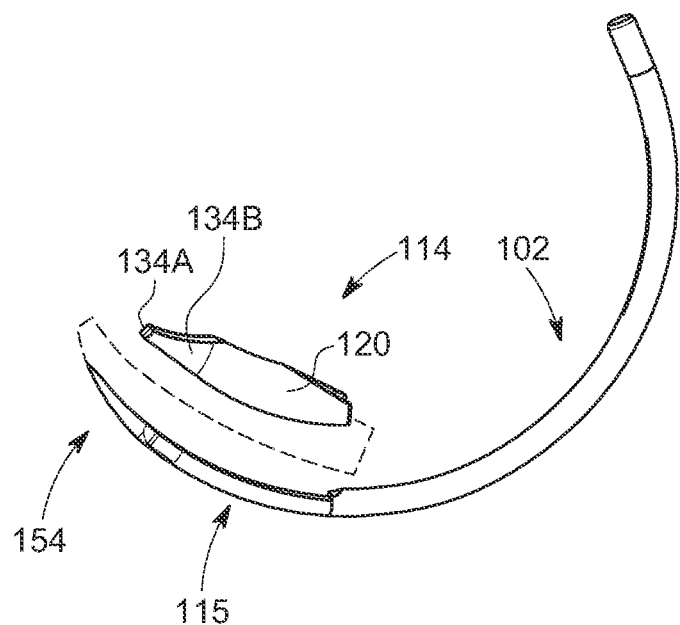
FIG. 6A is a side view of the first tissue anchor of FIGS. 2A-2F juxtaposed with the distal end of the insertion tool shown in FIGS. 5A-5F.
Figure 6B:
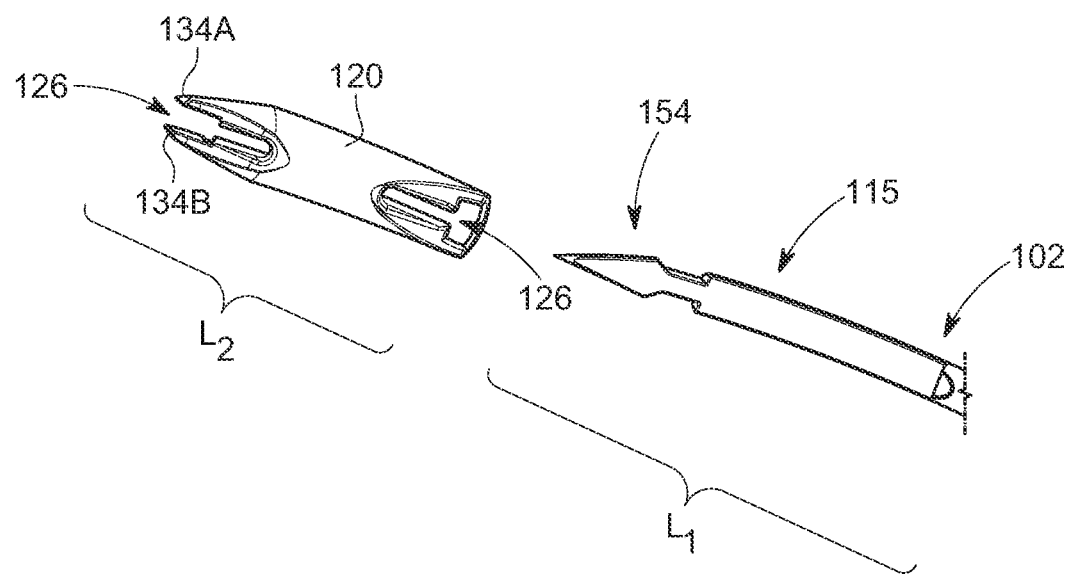
FIG. 6B is a top perspective view of the first tissue anchor and the distal end of the insertion tool shown in FIG. 6A.
Figure 6C:
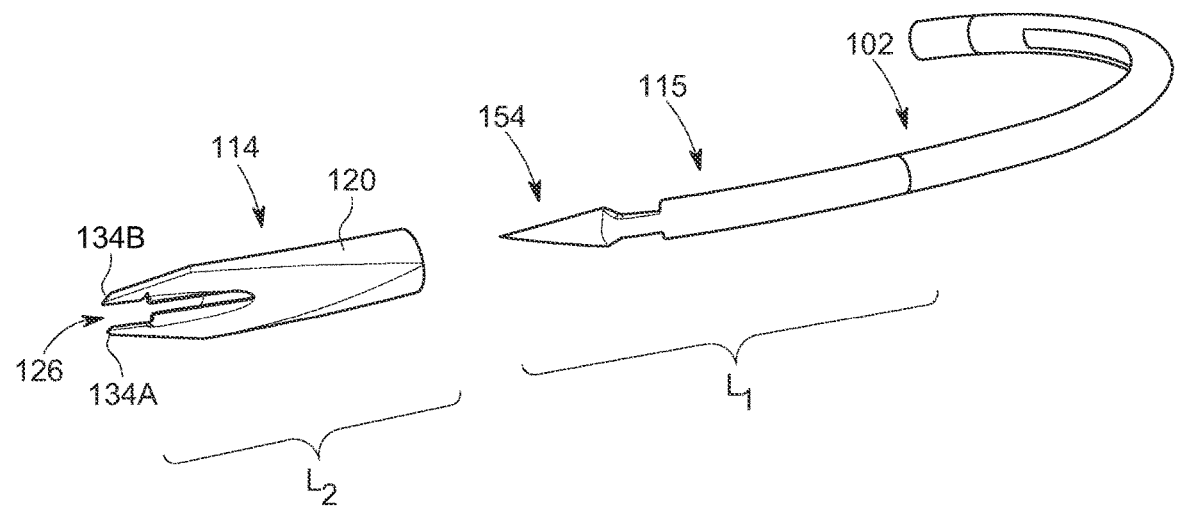
FIG. 6C is a bottom perspective view of the first tissue anchor and the insertion tool shown in FIGS. 6A and 6B.

Referring to FIGS. 6A-6C, in one embodiment, the first tissue anchor 114 is adapted to be secured to the curved distal section 115 of the insertion tool 102. In one embodiment, the hollow body or elongated body 120 of the first tissue anchor 114 preferably has a curved shape that matches the curved shape of the curved distal section 115 of the insertion tool 102. In one embodiment, the curved distal section 115 of the insertion tool 102 has a length L₁ that is greater than the length L₂ (FIG. 6B) of the first tissue anchor 114. In one embodiment, due to its greater length, the curved distal section 115 of the insertion tool 102 is adapted to pass completely through the insertion tool channel 126 of the first tissue anchor 114 so that the penetrating tip 154 of the insertion tool is distal to the spaced tips 134A, 134B of the first tissue anchor 114.

Figure 7:
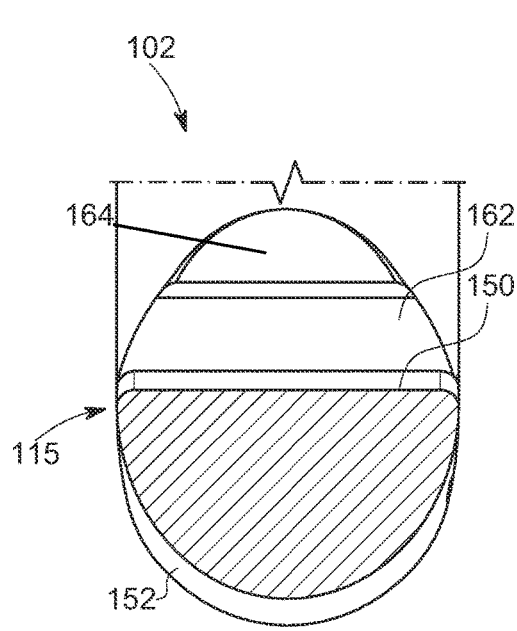
FIG. 7 is a cross-sectional view of the insertion tool shown in FIG. 5A taken along line 7-7 thereof.

Referring to FIG. 7, in one embodiment, the curved distal section 115 of the insertion tool 102 preferably has a cross-section having a semicircular shape including a flat surface 150 and a convexly curved underside 152. The proximal end of the curved distal section 115 is defined by the vertical wall 162 that acts as a hard stop for the first tissue anchor, and the sloping surface 164 that enables the filamentary element to pass between the proximal end of the first tissue anchor and the thicker portion of the insertion tool.

In one embodiment, the semicircular cross-sectional shape of the curved distal section 115 of the insertion tool 102 is adapted to conform to the cross-sectional shape of the insertion tool channel 126 (FIG. 2E) that extends through the hollow body of the first tissue anchor 114 (FIG. 1). In other embodiments, however, the curved distal section of the insertion tool may have a square, rectangular, trapezoidal, or any other cross-sectional shape that facilitates a secure fit between the tissue anchor and the insertion tool.

Figure 8:
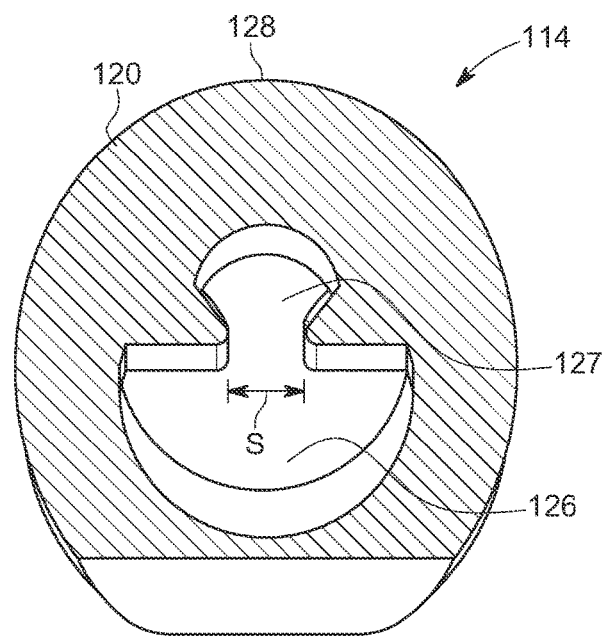
FIG. 8 is a cross-sectional view of the first tissue anchor shown in FIG. 2B taken along line 8-8 thereof.

Referring to FIG. 8, in one embodiment, the first tissue anchor 114 preferably includes the hollow body 120 having the insertion tool channel 126 that extends from the proximal end to the distal end of the hollow body. In one embodiment, the insertion tool channel 126 is curved to match the curve of the curved distal section 115 (FIG. 6A) of the insertion tool. In one embodiment, the insertion tool channel 126 has a semicircular cross-sectional shape that matches the semicircular cross-sectional shape of the curved distal section 115 of the insertion tool 102 (FIG. 7). In other embodiments, however, the insertion tool channel may have a square, rectangular, trapezoidal, or any other cross-sectional shape that facilitates a secure fit between the tissue anchor and the insertion tool.

In one embodiment, the first tissue anchor 114 preferably includes a filamentary element channel 127 that is located above the upper end of the insertion tool channel 126. In one embodiment, the filamentary element channel is located between the upper end of the insertion tool channel 126 and the top side 128 of the hollow body 120 of the first tissue anchor 114. In one embodiment, a filamentary element is preferably passed through the filamentary element channel 127 and wrapped around the closed top side 128 of the hollow body for connecting the first tissue anchor 114 to the filamentary element. In one embodiment, the filamentary element channel 127 (FIG. 8) may be open to the insertion tool channel 126 to further reduce the overall profile of the anchor, with the opening dimensioned such that the filamentary element 108 cannot inadvertently enter the insertion tool channel.

In one embodiment, the spacing S between the opposing side walls of the filamentary element channel 127 is less than the diameter of a filament (e.g., a suture thread) that passes through the filamentary element channel 127 to keep the filament captured within the filamentary element channel 127 and prevent the filament from moving into the insertion tool channel 126 of the hollow body 120.

Referring to FIGS. 9A-9F, in one embodiment, the curved distal section 115 of the insertion tool 102 is passed completely through the insertion tool channel 126 (FIG. 8) of the hollow body 120 of the first tissue anchor 114 so that the penetrating tip 154 at the distal end 106 of the insertion tool 102 is distal to the spaced tips 134A, 134B (FIG. 2A) located at the distal end of the first tissue anchor 114. When the first tissue anchor 114 has been secured onto the curved distal section 115 of the insertion tool 102, the spaced tips 134A, 134B of the first tissue anchor 114 are preferably seated within the respective notches 158A, 158B (FIG. 5C) formed in the sides of the curved distal section of the insertion tool, which define the neck 160 of the curved distal section 115. The spaced tips 134A, 134B are preferably seated within the notches 158A, 158B formed in the sides of the insertion tool, and the distal-most ends of the spaced tips 134A, 134B preferably abut against the respective sloping surfaces 165A, 165B that slope outwardly between the narrower width neck 160 and that wider proximal end 157 of the penetrating tip 154. The spaced tips 134A, 134B preferably form an interference fit with the respective notches 158A, 158B so that the first tissue anchor is releasably secured to the curved distal section 115 of the insertion tool 102.

Figure 9A:
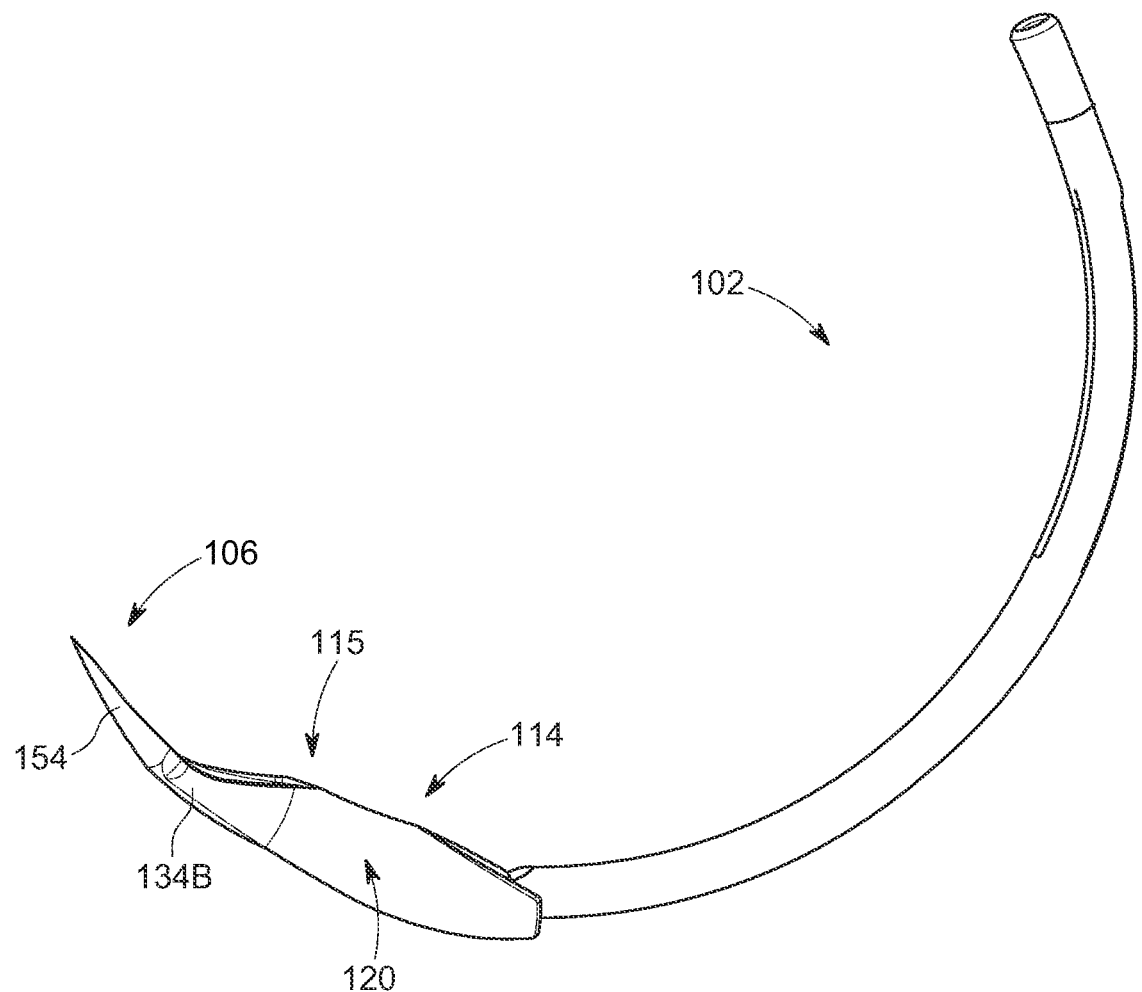
FIG. 9A is a side view of first tissue anchor of FIGS. 2A-2F after it has been secured to the distal end of the insertion tool of FIGS. 5A-5F, in accordance with one embodiment of the present patent application.
Figure 9B:
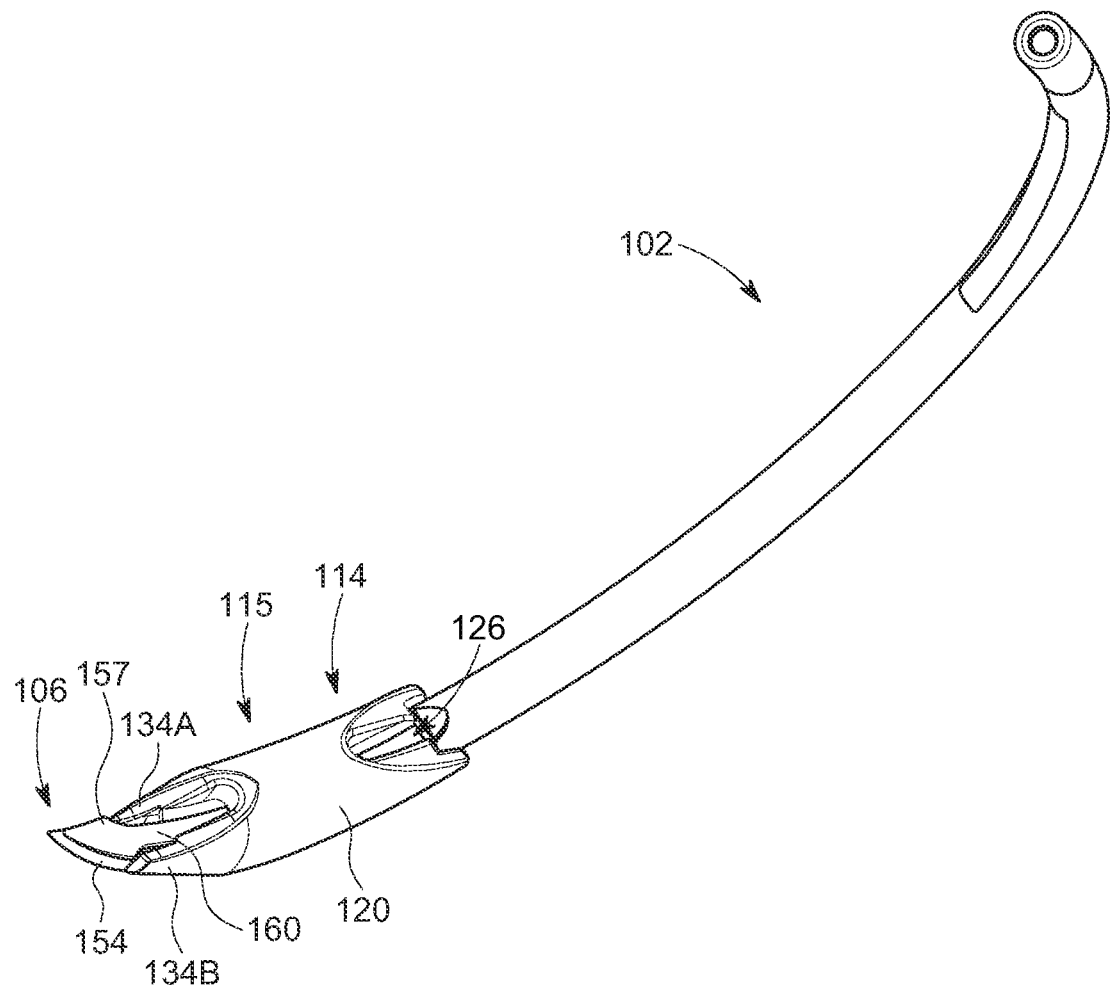
FIG. 9B is a perspective view of the first tissue anchor and the insertion tool shown in FIG. 9A.
Figure 9C:
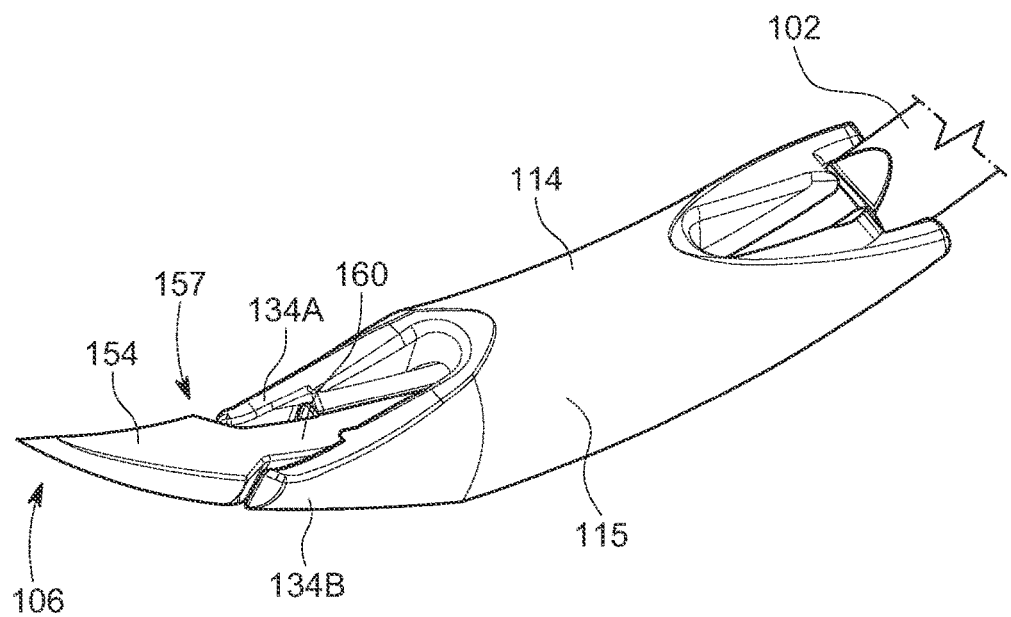
FIG. 9C is a magnified view of the first tissue anchor (partially transparent) and the distal end of the insertion tool shown in FIGS. 9A-9B.
Figure 9D:
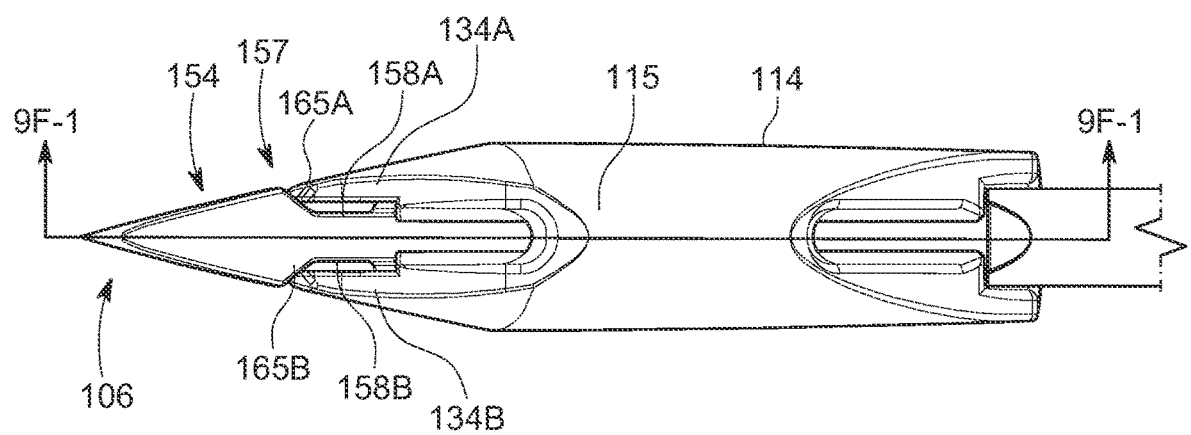
FIG. 9D is a top view of the first tissue anchor (partially transparent) and the distal end of the insertion tool shown in FIGS. 9A-9C.
Figure 9E:
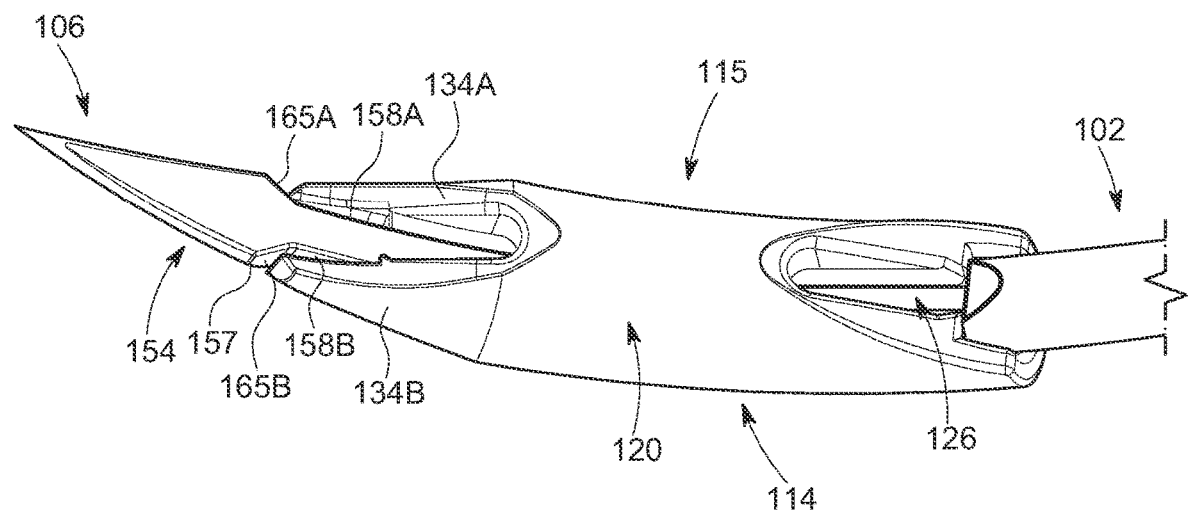
FIG. 9E is another perspective view of the first tissue anchor and the distal end of the insertion tool shown in FIGS. 9A-9D.
Figure 9F:
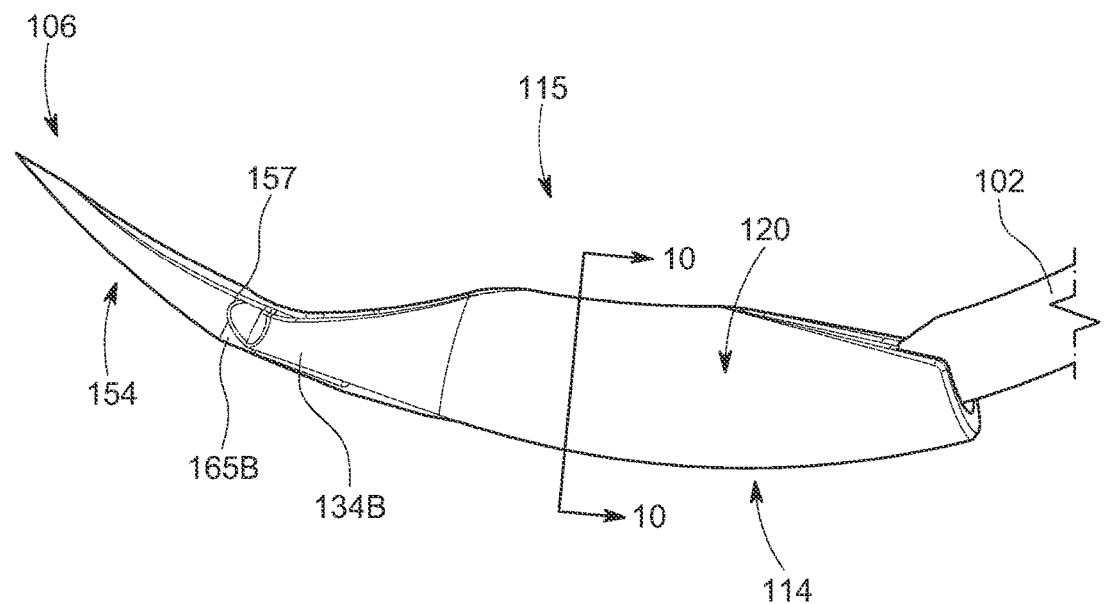
FIG. 9F is a side view of the first tissue anchor and the distal end of the insertion tool shown in FIGS. 9A-9E.
Figures 1, 9F:
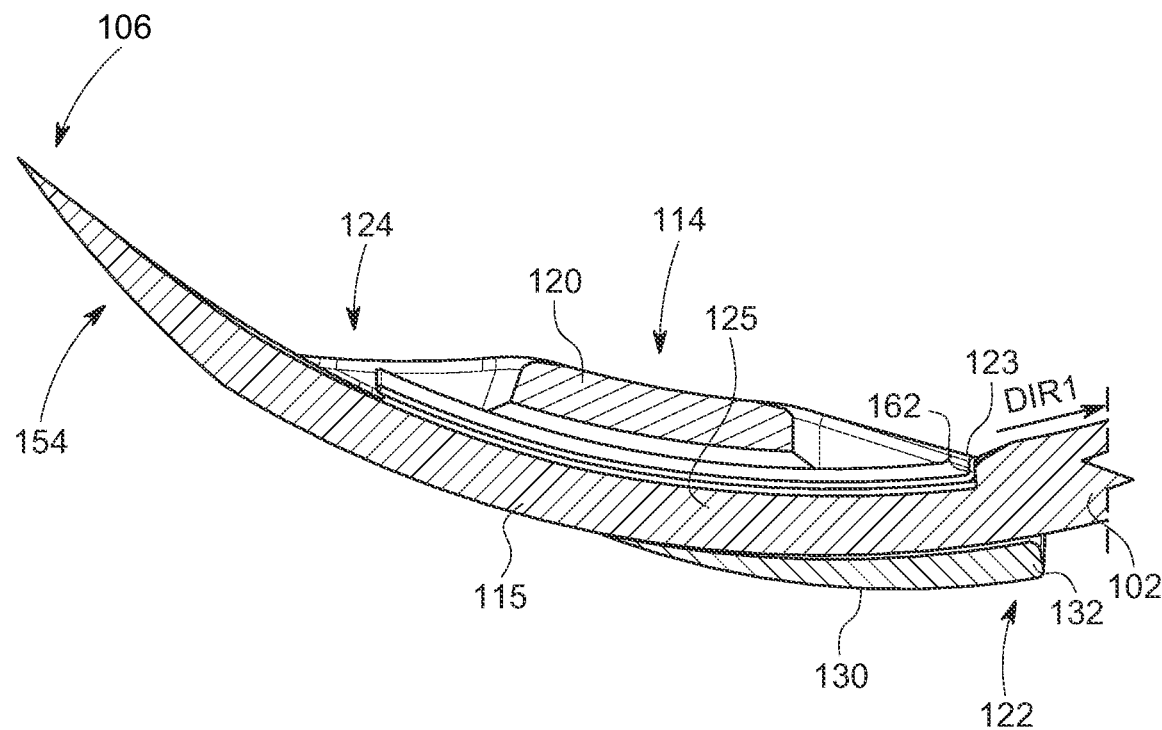
Figures 2, 9F:
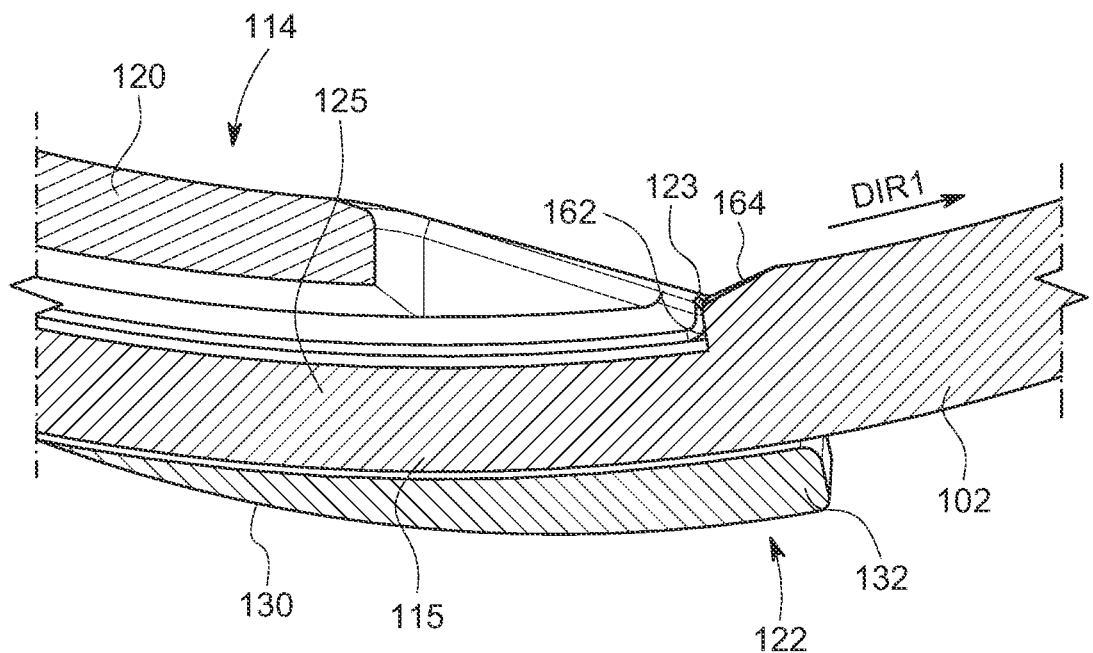

Referring to FIGS. 9F-1 and 9F-2, in one embodiment, the curved distal section 115 of the insertion tool 102 extends completely through the insertion tool channel 126 of the hollow body 120 of the first tissue anchor 114 so that the penetrating tip 154 of the insertion tool 102 is distal to the distal end 124 of the first tissue anchor 114. In one embodiment, the hollow body 120 of the first tissue anchor 114 is preferably aligned with the anchor seating section 125 of the curved distal section 115 of the insertion tool 102.

In one embodiment, the proximal end 122 of the hollow body 120 of the first tissue anchor 114 preferably includes the back wall 132 that is accessible below an underside of the curved distal section 115 of the insertion tool 102. In one embodiment, after the first tissue anchor 114 is implanted in tissue, when the insertion tool is retracted from the tissue, the back wall 132 of the hollow body 120 preferably engages the tissue to release the first tissue anchor 114 from the curved distal section 115 of the insertion tool 102.

In one embodiment, the proximal end of the first tissue anchor seating section 125 includes the vertical wall 162 that is adapted to engage a proximal surface 123 of the hollow body 120 of the first tissue anchor 114 for preventing the first tissue anchor from sliding proximally in the direction DIR1 relative to the vertical wall 162. Thus, the vertical wall 162 acts as a stop that halts proximal movement of the first tissue anchor after the proximal surface 123 of the first tissue anchor 114 has contacted the vertical wall. The insertion tool 102 preferably includes the sloping surface 164 that is adapted to accommodate a filamentary element that passes through the hollow body of the first tissue anchor 114.

In one embodiment, a portion of the underside or bottom surface 130 of the elongated body 120 of the first tissue anchor 114 is removed to minimize the cross-sectional dimension of the elongated body. In one embodiment, the material that is removed from the underside of the elongated body 120 conforms the underside of the first tissue anchor 114 with the convexly curved surface of the bottom of the insertion tool 102, thereby minimizing drag forces as the first tissue anchor is implanted in tissue.

Figure 10:
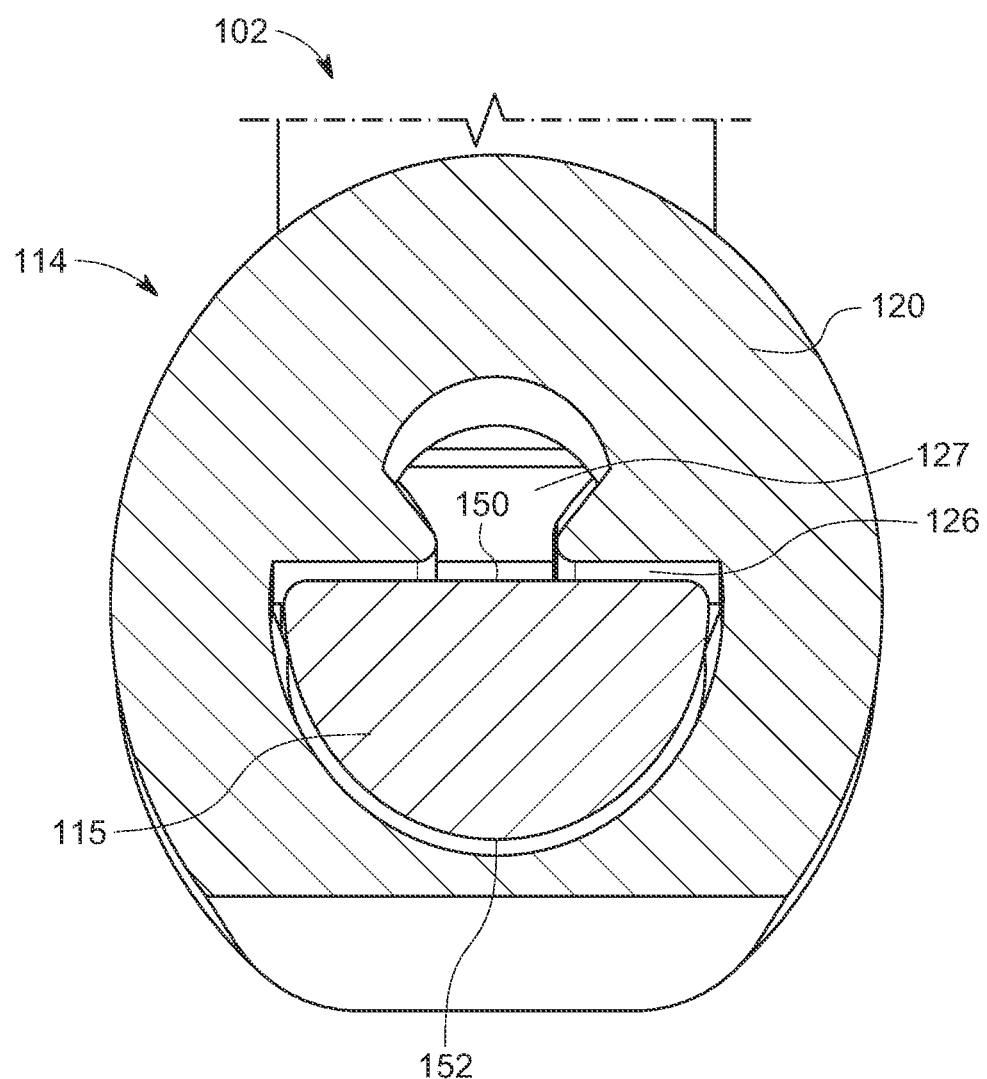
FIG. 10 is a cross-sectional view of the first tissue anchor and the insertion tool of FIGS. 9A-9F taken along line 10-10 of FIG. 9F.

Referring to FIG. 10, in one embodiment, the first tissue anchor 114 is secured onto the curved distal section 115 of the insertion tool 102. The curved distal section 115 of the insertion tool preferably has a cross-section that defines a semicircular shape including a flat top surface 150 and a convexly curved underside surface 152 that preferably matches the semicircular shaped cross-section of the insertion tool channel 126 that extends along the length of the hollow body 120 of the first tissue anchor 114. After the first tissue anchor is releasably secured to the distal end of the insertion tool, the matching semicircular shapes of the first tissue anchor and the insertion tool prevent the first tissue anchor from twisting and/or rotating about its long axis relative to the distal end of the insertion tool. The filamentary element channel 127 preferably extends over the upper end of the insertion tool channel 126 for accommodating the filamentary element that is coupled with the first tissue anchor.

Figure 11A:
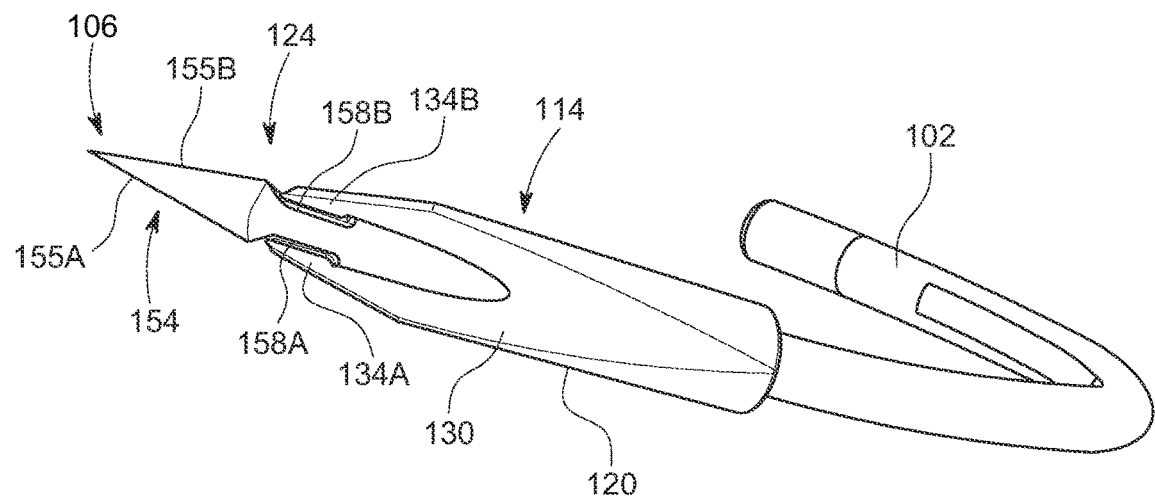
FIG. 11A is a perspective view of the bottom of the first tissue anchor and the insertion tool shown in FIGS. 9A-9F.
Figure 11B:
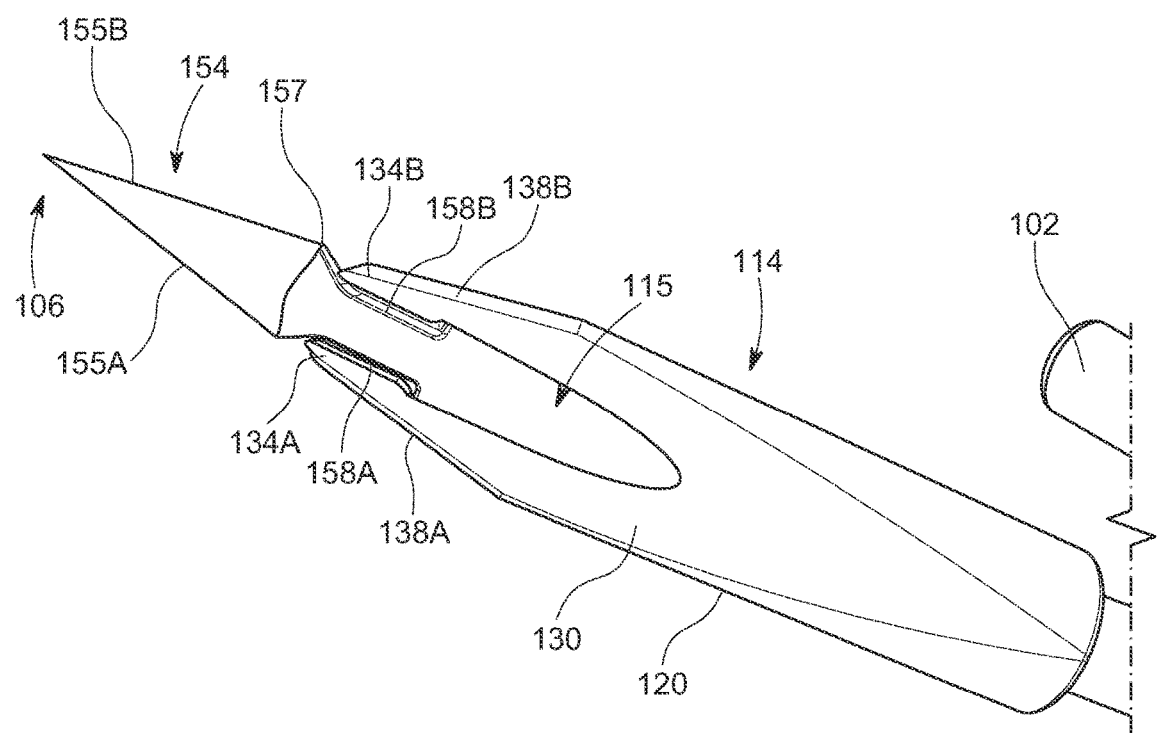
FIG. 11B is a magnified view of the first tissue anchor and the distal end of the insertion tool shown in FIG. 11A.

Referring to FIGS. 11A and 11B, in one embodiment, the first tissue anchor 114 may be secured to the curved distal section 115 of the insertion tool 102. The penetrating tip 154 of the insertion tool 102 preferably extends beyond the distal end 124 of the elongated body 120 of the first tissue anchor 114. In one embodiment, material is removed from the underside 130 of the elongated body 120 for minimizing the cross-sectional profile of the first tissue anchor 114 and for conforming the shape of the underside of the elongated body 120 to the convexly curved underside of the curved distal section 115 of the insertion tool 102, which minimizes drag as the tissue anchor is advanced through tissue.

In one embodiment, the first tissue anchor 114 preferably has the spaced tips 134A, 134B that are located at the distal end of the hollow body 120 of the first tissue anchor, which are preferably seated within the respective lateral notches 158A, 158B that are formed in the sides of the curved distal section 115 of the insertion tool 102. The outer surfaces 138A, 138B of the respective spaced tips 134A, 134B preferably slope inwardly so that the distal most ends of the tips 138A, 138B are protected by relatively wider width of the penetrating tip 154 at the proximal end 157 of the penetrating tip 154, which facilitates passing the first tissue anchor through tissue. In one embodiment, the penetrating tip 154 tapers outwardly from a distal point 156 so that the penetrating tip may be used to form a pathway in tissue, with the first tissue anchor following the penetrating tip along the pathway for being implanted in the tissue.

In one embodiment, the contour or slope of the outer surfaces 138A, 138B of the respective spaces tips 134A, 134B preferably conform to the taper or slope of the respective leading edges 155A, 155B of the penetrating tip 154 so that that leading ends of the spaced tips 134A, 134B are shrouded and/or protected by the leading edges 155A, 155B of the penetrating tip 154 as the penetrating tip leads the first tissue anchor 114 through tissue. In one embodiment, when the insertion tool 102 is inserted through tissue, the flexible tips deflect inwardly, thereby facilitating ease of penetration and mitigating potential tissue entrapment between the tissue anchor and the insertion tool.

Figure 12:
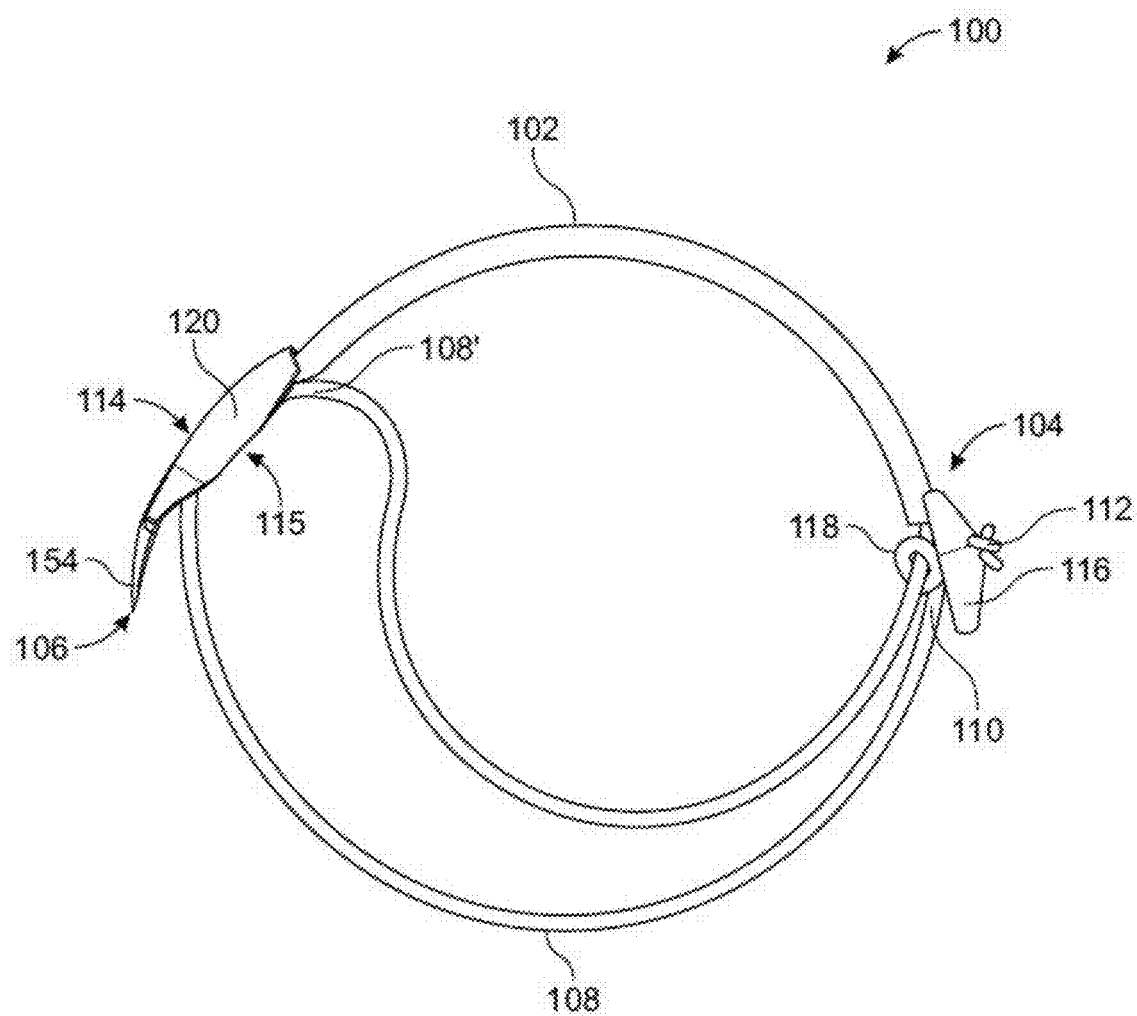
FIG. 12 is a schematic view of a wound closure assembly including an insertion tool, a first tissue anchor releasably secured to a distal end of the insertion tool, a second tissue anchor, and a filamentary element having a slip knot, in accordance with one embodiment of the present patent application.

Referring to FIG. 12, in one embodiment, the wound closure assembly 100 preferably includes the insertion tool 102 having a curved, elongated body with a curved distal section 115 (FIG. 6A) that terminates at the distal end 106 of the insertion tool, and a proximal end 104 that is secured to a first end 110 of the filamentary element 108. The wound closure assembly 100 preferably includes the filamentary element 108 and the first tissue anchor 114 coupled with the closed end loop 108' of the filamentary element. In one embodiment, the first tissue anchor is free to slide and/or toggle relative to the closed end loop 108' of the filamentary element. The distal end 106 of the insertion tool 102 extends completely through the insertion tool channel of the elongated body 120 of the first tissue anchor 114 so that the penetrating tip 154 at the distal end 106 of the insertion tool 102 is distal to the spaced tips at the distal end of hollow body 120 of the first tissue anchor 114.

The wound closure assembly 100 preferably includes the second tissue anchor 116 that is fixedly secured to the second end 112 of the filamentary element 108 via a fixed knot. The wound closure assembly 100 preferably includes the slip knot 118 that is positioned between the first and second tissue anchors 114, 116, whereby the distance between the tissue anchors may be reduced by pulling on the first end 110 of the filamentary element 108 (e.g., by pulling the insertion tool 102 away from the first tissue anchor 114 after the first tissue anchor is implanted in tissue).

FIGS. 13A-13H illustrate various steps of a surgical method of using the wound closure assembly 100 disclosed herein to approximate first and second tissue planes 190, 192.

Figure 13A:
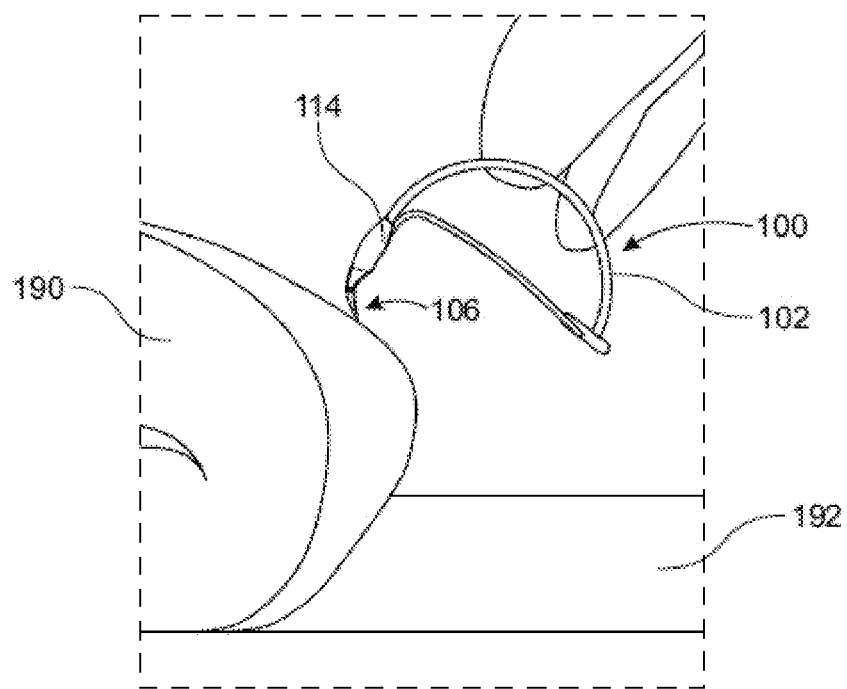
FIG. 13A illustrates a first stage of a method of drawing two tissue layers together, in accordance with one embodiment of the present patent application.

Referring to FIG. 13A, in one embodiment, the distal end 106 of the insertion tool 102 is positioned within the insertion tool channel 126 (FIG. 9F-1) of the first tissue anchor 114 of a wound closure assembly 100. In one embodiment, a surgeon may use a clamping tool to grasp the curved insertion tool 102, and the insertion tool is positioned so that the distal penetrating tip 154 (FIG. 6B) of the insertion tool 102 is close to a first tissue flap 190.

Figure 13B:
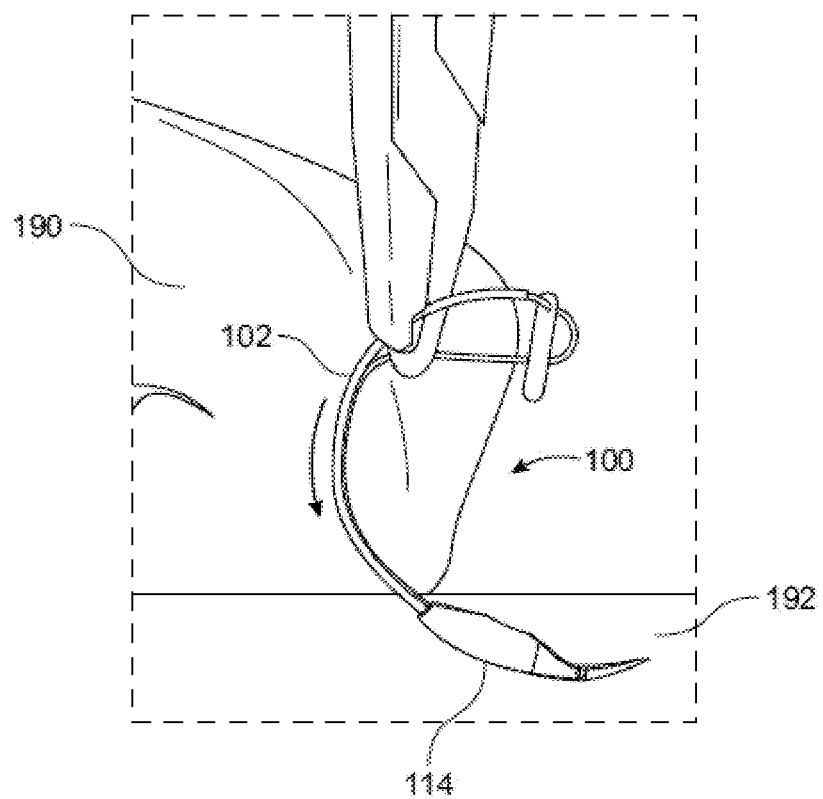
FIG. 13B illustrates a second stage of a method of drawing two tissue layers together, in accordance with one embodiment of the present patent application.
Figure 13C:
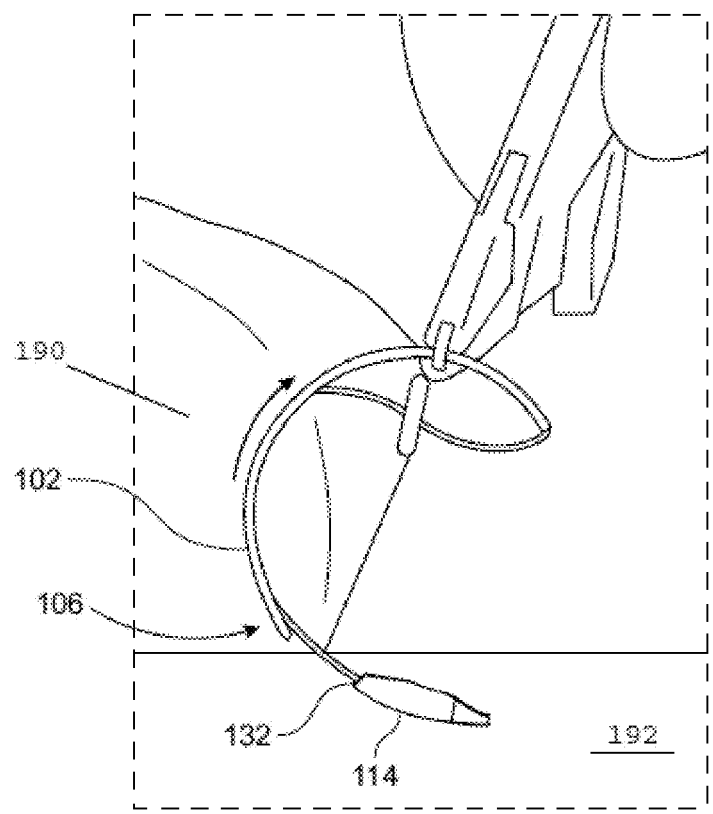
FIG. 13C illustrates a third stage of a method of drawing two tissue layers together, in accordance with one embodiment of the present patent application.

Referring to FIG. 13B, in one embodiment, the insertion tool 102 is used to insert the first tissue anchor 114 of the wound closure assembly 100 through the first tissue flap 190 and into a second tissue plane 192 so that the first tissue anchor 114 is disposed within the second tissue plane 192.

Figure 13D:
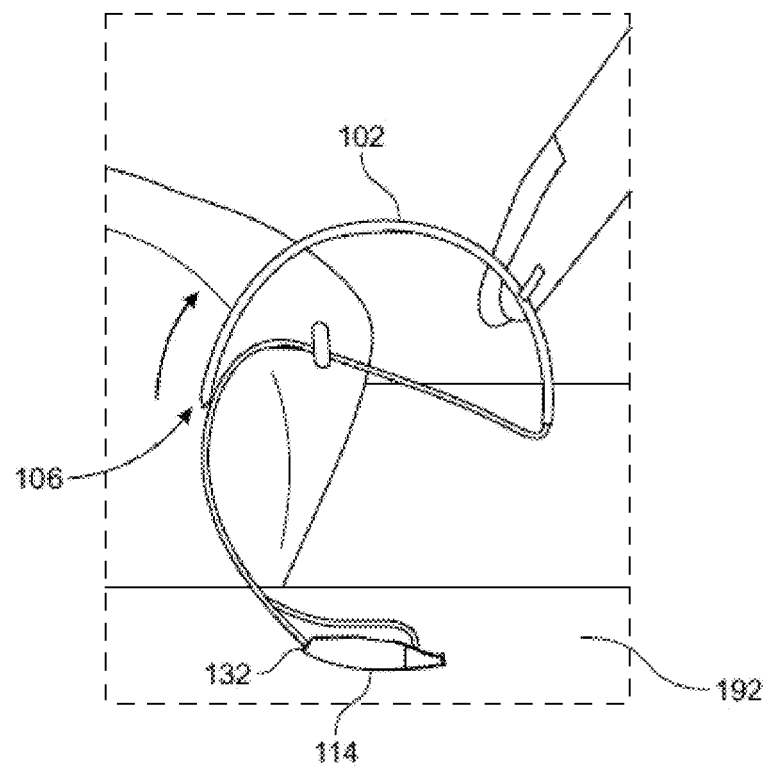
FIG. 13D illustrates a fourth stage of a method of drawing two tissue layers together, in accordance with one embodiment of the present patent application.

Referring to FIGS. 13O and 13D, in one embodiment, after the first tissue anchor 114 is embedded within the second tissue plane 192, the curved insertion tool 102 may be retracted in the direction shown by the arrow for disconnecting the first tissue anchor from the insertion tool. In one embodiment, the retraction of the insertion tool 102 shown in FIGS. 13C-13E may be done as part of a single, continuous motion.

Figure 13E:
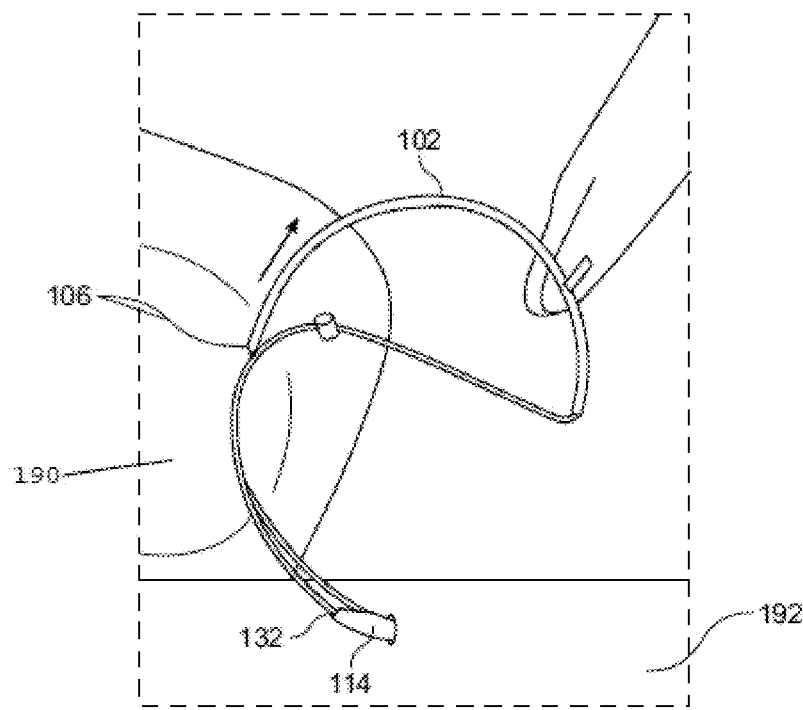
FIG. 13E illustrates a fifth stage of a method of drawing two tissue layers together, in accordance with one embodiment of the present patent application.

Referring to FIGS. 13D and 13E, in one embodiment, as the insertion tool 102 is retracted from the tissue in the direction of the arrow, the back wall 132 of the hollow body of the first tissue anchor 114 preferably engages the tissue within the second tissue plane 192 for detaching the first tissue anchor 114 from the distal end 106 of the insertion tool 102. After the first tissue anchor 114 is detached from the insertion tool 102, the first tissue anchor 114 remains embedded within the second tissue plane 192.

Figure 13F:
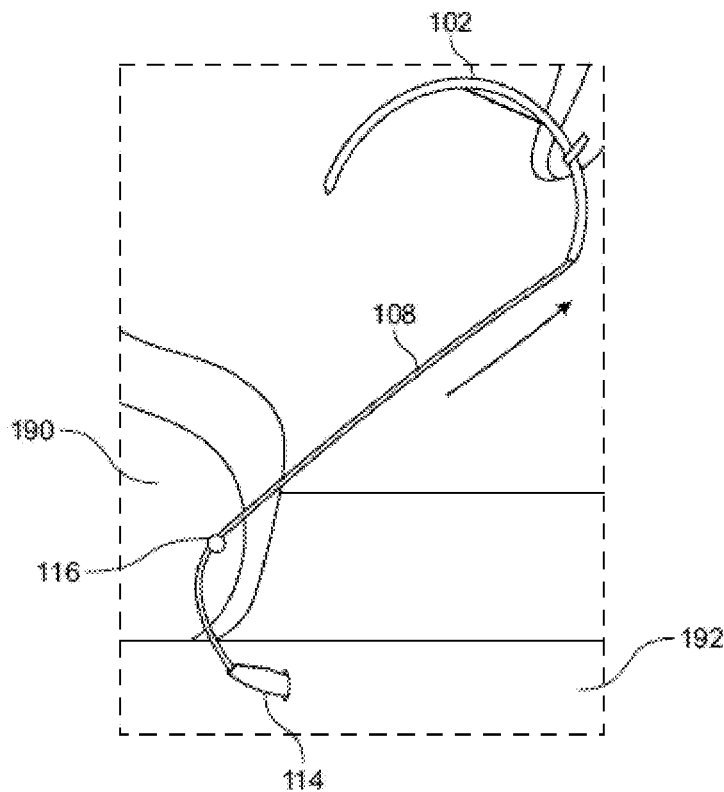
FIG. 13F illustrates a sixth step of a method of drawing two tissue layers together, in accordance with one embodiment of the present patent application.

Referring to FIG. 13F, once the insertion tool 102 is entirely retracted from the second tissue plane 192 and the first tissue flap 190, the insertion tool is pulled in the direction indicated by the arrow, which, due to the presence of the slip knot 118 (FIG. 12) formed in the filamentary element 108 between the first and second tissue anchors 114, 116, causes the second tissue anchor 116 to be drawn closer to the first tissue anchor 114 to thereby draw the first tissue flap 190 toward the second tissue plane 192.

Figure 13G:
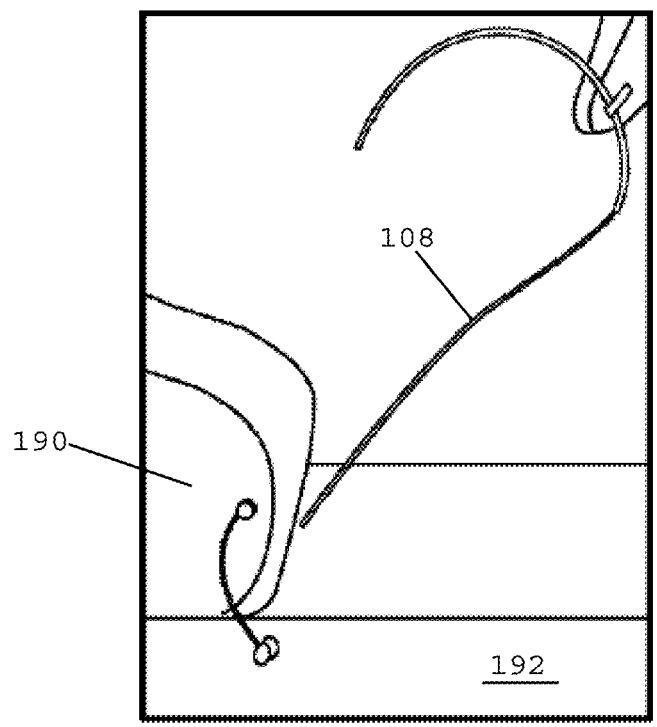
FIG. 13G illustrates a seventh stage of a method of drawing two tissue layers together, in accordance with one embodiment of the present patent application.
Figure 13H:
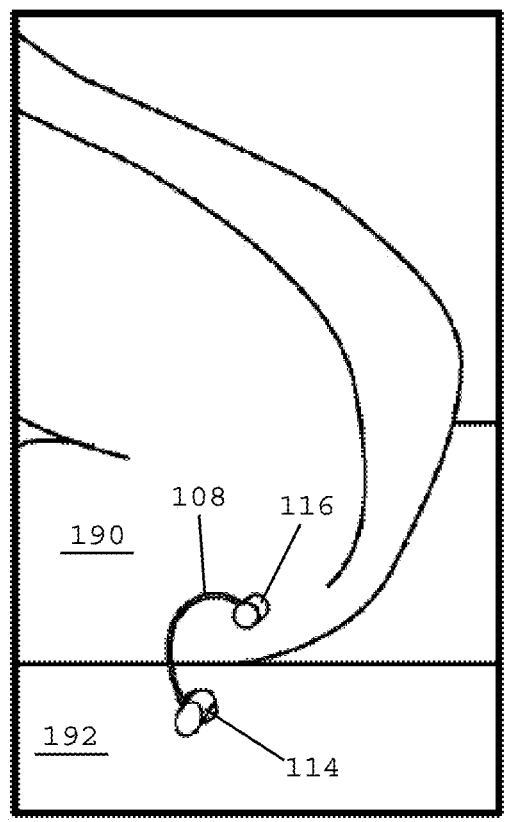
FIG. 13H illustrates an eighth stage of a method of drawing two tissue layers together, in accordance with one embodiment of the present patent application.

Referring to FIG. 13G, in one embodiment, the filamentary element 108 may be cut in proximity to the first tissue flap 190, which leaves the first tissue anchor 114, the second tissue anchor 116, and the uncut section of the filamentary element 108 implanted in the tissue for approximating the first tissue flap 190 with the second tissue plane 192.

Figure 14A:
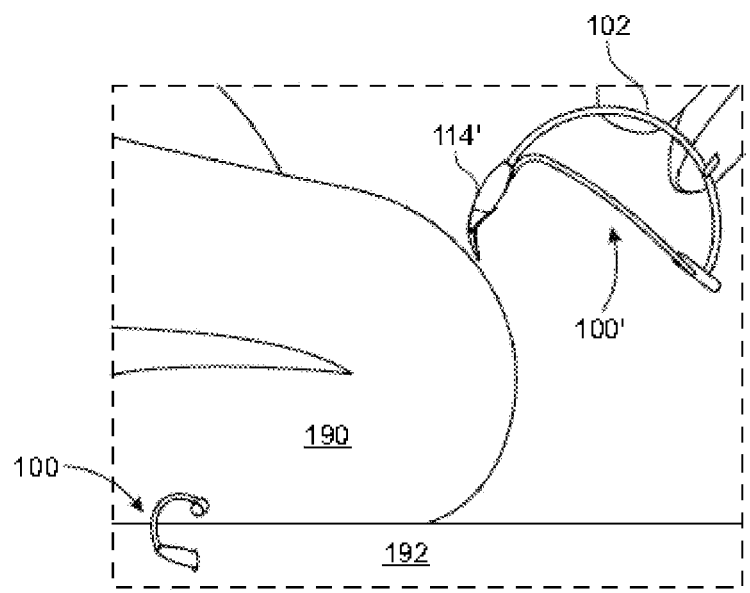
FIG. 14A illustrates a first stage of a method of implanting a second wound closure assembly for drawing two tissue layers together, in accordance with one embodiment of the present patent application.
Figure 14B:
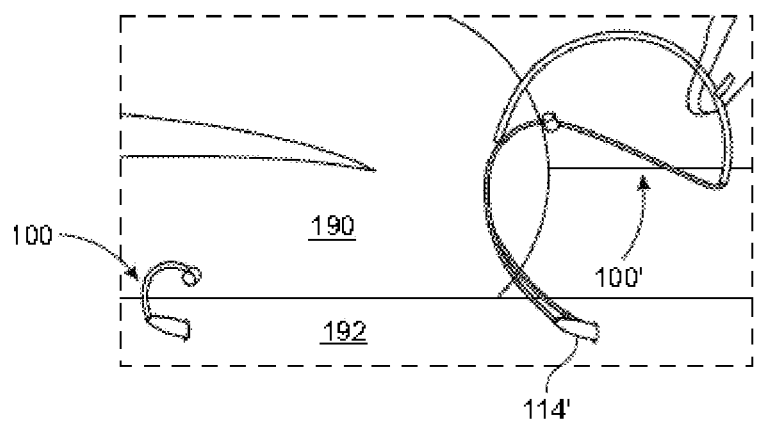
FIG. 14B illustrates a second stage of a method of implanting a second wound closure assembly for drawing two tissue layers together, in accordance with one embodiment of the present patent application.
Figure 14C:
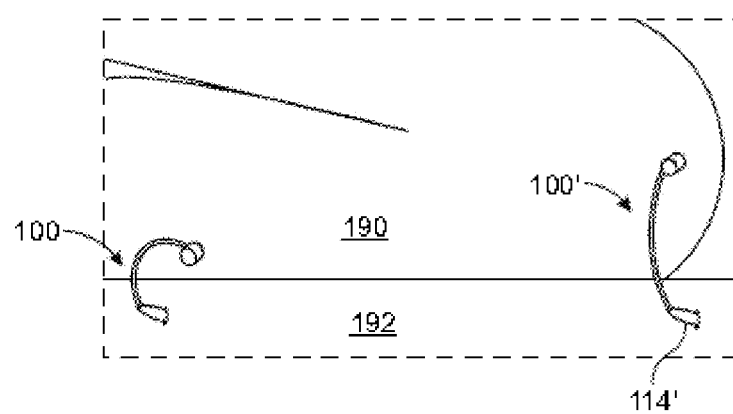
FIG. 14C illustrates a third stage of a method of implanting a second wound closure assembly for drawing two tissue layers together, in accordance with one embodiment of the present patent application.

Referring to FIGS. 14A-14C, in one embodiment, an additional wound closure assembly 100' may be implanted adjacent the first wound closure assembly 100 to further approximate the first tissue flap 190 with the second tissue plane 192. In one embodiment, additional wound closure assemblies (e.g., 10, 20, 30, or more) may be implanted at successive intervals along the length of the first tissue flap 190 and the second tissue plane 192 for approximating the adjacent tissue layers.

In one embodiment, the wound closure assembly disclosed in the present patent application preferably enables secure and quick tissue plane approximation that greatly reduces fluid buildup and the resulting risk of seroma formation.

In one embodiment, the wound closure assembly may be implanted by a surgeon using a single hand and using familiar techniques (e.g. using common needle holders), leaving the other hand free to maintain positioning and tension on tissue (e.g., a tissue flap).

In one embodiment, the wound closure assembly disclosed herein provides for greatly increased speed over known progressive tissue suturing (PTS) or suture quilting techniques with each wound closure assembly taking approximately five-ten (5-10) seconds, and more preferably about six (6) seconds to implant.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A wound closure assembly comprising:
   an insertion tool having a proximal end and a distal end including a distal section having a penetrating tip at a distal-most end of said insertion tool and first and second notches that are proximal to said penetrating tip and that are formed on opposite sides of said distal section;
   a tissue anchor including a hollow body having a proximal end, a distal end, an insertion tool channel extending through said hollow body, and first and second spaced tips that project distally from the distal end of said hollow body and that oppose one another on opposite sides of said insertion tool channel, wherein said distal section of said insertion tool is inserted into said insertion tool channel of said tissue anchor so that said penetrating tip is distal to said first and second spaced tips, and wherein said first and second spaced tips are nested within said respective first and second notches of said insertion tool for generating a releasable interference fit between said first and second spaced tips of said tissue anchor and said distal section of said insertion tool.

2. The wound closure assembly as claimed in claim 1, wherein said distal section of said insertion tool is curved, and wherein said hollow body of said tissue anchor has a curved configuration that matches the curvature of said curved distal section of said insertion tool.

3. The wound closure assembly as claimed in claim 2, wherein said insertion tool channel of said tissue anchor has a curved configuration that matches the curvature of said curved distal section of said insertion tool.

4. The wound closure assembly as claimed in claim 2, wherein said curved distal section of said insertion tool comprises:
   said penetrating tip that defines the distal-most end of said insertion tool;
   said first and second notches that are proximal to said penetrating tip are formed in respective first and second lateral sides of said curved distal section for defining a neck of said curved distal section;
   a tissue anchor seating surface that is proximal to said neck and that is adapted to seat said hollow body of said tissue anchor on said curved distal section of said insertion tool.

5. The wound closure assembly as claimed in claim 4, wherein said penetrating tip comprises a distal end that defines a distal piercing point and a proximal end that is connected to a distal end of said neck, and wherein said penetrating tip has lateral surfaces that taper outwardly between said distal piercing point and the proximal end of said penetrating tip.

6. The wound closure assembly as claimed in claim 5, wherein said neck of said curved distal section has a first laterally extending width and the proximal end of said penetrating tip has a second laterally extending width that is greater than the first laterally extending width of said neck.

7. The wound closure assembly as claimed in claim 6, wherein said curved distal section further comprises a first sloping surface on the first lateral side of said curved distal section that slopes outwardly from the distal end of said neck to the proximal end of said penetrating tip and a second sloping surface on the second lateral side of said curved distal section that slopes outwardly from the distal end of said neck to the proximal end of said penetrating tip.

8. The wound closure assembly as claimed in claim 6, wherein said tissue anchor seating surface has a third laterally extending width that is greater than the first laterally extending width of said neck.

9. The wound closure assembly as claimed in claim 1, wherein said distal section of said insertion tool has a cross-sectional dimension having a semicircular shape and said insertion tool channel of said tissue anchor has a cross-sectional dimension having a semicircular shape that matches the semicircular shape of said distal section of said insertion tool.

10. The wound closure assembly as claimed in claim 1, further comprising:
- a filamentary element having a first end secured to the proximal end of said insertion tool and a second end remote from the first end of said filamentary element;
- said tissue anchor being coupled to said filamentary element between the first and second ends of said filamentary element;
- a second tissue anchor secured to the second end of said filamentary element;
- said filamentary element including a slip knot that is located between said first and second tissue anchors that enables a distance between said first and second tissue anchors to be decreased by pulling on the first end of said filamentary element via said insertion tool.

11. A wound closure assembly comprising:
- an insertion tool having a proximal end and a distal section, wherein said distal section includes a penetrating tip and first and second notches formed on opposing sides of said distal section;
- a first tissue anchor including a hollow body having a proximal end, a distal end, and an insertion tool channel extending from the proximal end to the distal end of said hollow body, said hollow body including first and second spaced tips that project distally from the distal end of said hollow body and that oppose one another on opposite sides of the insertion tool channel, wherein said distal section of said insertion tool is inserted into said insertion tool channel so that said penetrating tip is distal to said first and second spaced tips and said first and second spaced tips are seated within said respective first and second notches for generating a releasable interference fit between said first and second spaced tips and said distal section of said insertion tool;
- a filamentary element having a first end secured to the proximal end of said insertion tool and a second end remote from the first end;
- a second tissue anchor secured to said filamentary element adjacent the second end of said filamentary element; and
- said filamentary element including a slip knot that is located between said first and second tissue anchors for enabling a distance between said first and second tissue anchors to be decreased by pulling on the first end of said filamentary element via said insertion tool.

12. The wound closure assembly as claimed in claim 11, wherein said distal section of said insertion tool is curved, and wherein said insertion tool channel of said hollow body of said first tissue anchor has a curved configuration that matches the curvature of said curved distal section of said insertion tool.

13. The wound closure assembly as claimed in claim 12, wherein said curved distal section of said insertion tool comprises:
- said penetrating tip that defines a distal-most end of said insertion tool;
- said first and second notches that are proximal to said penetrating tip are formed in respective first and second lateral sides of said curved distal section for defining a neck of said curved distal section;
- a first tissue anchor seating surface that is proximal to said first and second notches and that is adapted to seat said hollow body of said first tissue anchor.

14. The wound closure assembly as claimed in claim 13, wherein said penetrating tip comprises a distal end that defines a distal piercing point at a distal-most end of said insertion tool and a proximal end that is connected to a distal end of said neck, and wherein said penetrating tip has lateral surfaces that taper outwardly from said distal piercing point to the proximal end of said penetrating tip.

15. The wound closure assembly as claimed in claim 14, wherein said neck of said curved distal section has a first laterally extending width and the proximal end of said penetrating tip has a second laterally extending width that is greater than the first laterally extending width of said neck.

16. The wound closure assembly as claimed in claim 14, further comprising:
- a first sloping surface on the first lateral side of said curved distal section that slopes outwardly from the distal end of said neck to the proximal end of said penetrating tip; and
- a second sloping surface on the second lateral side of said curved distal section that slopes outwardly from the distal end of said neck to the proximal end of said penetrating tip, and wherein said first and second spaced tips of said first tissue anchor are shrouded by said first and second sloping surfaces that extend from the distal end of said neck to the proximal end of said penetrating tip.

17. The wound closure assembly as claimed in claim 11, wherein said distal section of said insertion tool has a cross-sectional dimension having a semicircular shape and said insertion tool channel of said first tissue anchor has a cross-sectional dimension having a semicircular shape that matches the semicircular shape of said distal section of said insertion tool.

18. The wound closure assembly as claimed in claim 14, wherein said insertion tool includes a stop located at a proximal end of said first tissue anchor seating surface that is adapted to engage a proximal surface of said hollow body of said first tissue anchor to halt movement of said hollow body toward the proximal end of said insertion tool.

19. The wound closure assembly as claimed in claim 11, wherein said insertion tool channel defines a first lateral width, and said first and second spaced tips have opposing inner surfaces that define a second lateral width that is smaller than the first lateral width of said insertion tool channel.

20. A kit comprising:
- a plurality of wound closure assemblies contained within a single package, wherein each said wound closure assembly further comprises
- an insertion tool having a proximal end and a distal section including a penetrating tip at a distal-most end of said insertion tool and first and second notches that are proximal to said penetrating tip and that are formed on opposite sides of said distal section; and
- a tissue anchor including a hollow body having a proximal end, a distal end, an insertion tool channel extending through said hollow body, and first and second spaced tips that project distally from the distal end of said hollow body and that oppose one another on opposite sides of said insertion tool channel, wherein said distal section of said insertion tool is inserted into said insertion tool channel of said tissue anchor so that said penetrating tip is distal to said first and second spaced tips, and wherein said first and second spaced tips are nested within said respective first and second notches of said insertion tool for generating a releasable interference fit between said first and second spaced tips of said tissue anchor and said distal section of said insertion tool.

21. The kit as claimed in claim 20, wherein each said wound closure assembly further comprises:

a filamentary element having a first end secured to the proximal end of said insertion tool and a second end remote from the first end;

said tissue anchor being slidably coupled to said filamentary element between the first and second ends of said filamentary element;

a second tissue anchor secured to the second end of said filamentary element;

said filamentary element including a slip knot that is located between said first and second tissue anchors that enables a distance between said first and second tissue anchors to be decreased by pulling on the first end of said filamentary element via said insertion tool.

\* \* \* \* \*